(12) United States Patent
Meier et al.

(10) Patent No.: US 8,987,285 B2
(45) Date of Patent: Mar. 24, 2015

(54) PHARMACEUTICAL COMPOSITIONS, DOSAGE FORMS AND NEW FORMS OF THE COMPOUND OF FORMULA (I), AND METHODS OF USE THEREOF

(75) Inventors: Ulrich Meier, Riehen (CH); Nicole Bieri, Muttenz (CH); Dieter Becker, Freiburg (DE); Julien Taillemite, Huningue (FR); Marie-Pierre Filliot, Geispitzen (FR); Tanja Meister, Rheinfelden (DE)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/990,632

(22) PCT Filed: Dec. 5, 2011

(86) PCT No.: PCT/EP2011/071821
§ 371 (c)(1),
(2), (4) Date: May 30, 2013

(87) PCT Pub. No.: WO2012/072824
PCT Pub. Date: Jun. 7, 2012

(65) Prior Publication Data
US 2013/0252979 A1    Sep. 26, 2013

Related U.S. Application Data

(60) Provisional application No. 61/419,567, filed on Dec. 3, 2010.

(51) Int. Cl.
| | | |
|---|---|---|
| *A01N 43/54* | (2006.01) | |
| *A61K 31/517* | (2006.01) | |
| *C07D 239/72* | (2006.01) | |
| *A61K 45/06* | (2006.01) | |
| *C07D 409/12* | (2006.01) | |

(52) U.S. Cl.
CPC .............. *A61K 31/517* (2013.01); *A61K 45/06* (2013.01); *C07D 409/12* (2013.01)
USPC ................... 514/266.1; 514/266.2; 544/283; 544/284

(58) Field of Classification Search
USPC ..................... 514/266.1, 266.2; 544/283, 284
See application file for complete search history.

(56) References Cited

FOREIGN PATENT DOCUMENTS

| WO | WO 2007056167 | * | 5/2007 |
| WO | WO 2008/137809 | * | 11/2008 |
| WO | WO 2010054020 | * | 5/2010 |

OTHER PUBLICATIONS

International Search Report, dated Apr. 4, 2012, in International Patent Application No. PCT/EP2011/071821.

* cited by examiner

*Primary Examiner* — Paul V. Ward
(74) *Attorney, Agent, or Firm* — Sheppard Mullin Richter & Hampton LLP

(57) ABSTRACT

The present invention relates to a novel crystalline anhydrous form of [(5-chlorothiophene-2-ylsulfonylcarbamoyl)-(4-(6-fluoro-7-(methylamino)-2,4-dioxo-1,2-dihydroquinazolin-3(4H)-yl)phenyl]amide, potassium salt, and its use in the treatment or prevention of a condition or a disorder with platelet ADP receptor inhibition, in particular, $P2Y_{12}$ inhibition, in animals, particularly humans. It also relates processes for making such a novel crystalline form. The present invention also relates to a solid, oral formulation of this novel crystalline form, its preparation and use thereof.

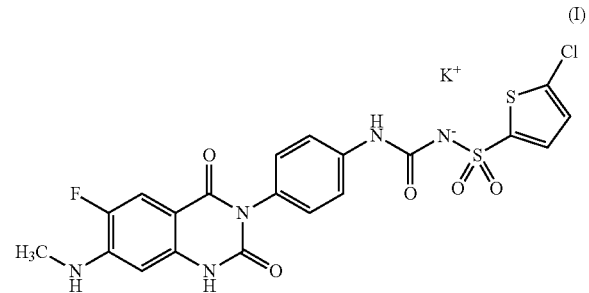

14 Claims, 8 Drawing Sheets

Solid state NMR spectrum of the anhydrous form of the compound of formula (I)

Multi pH Dissolution profile Elinogrel Film-coated tablets
(Example 7 and Example 8)

Dissolution profile pH 7.4 Elinogrel Film-coated tablets
(Example 7 and Example 8)

PHARMACEUTICAL COMPOSITIONS, DOSAGE FORMS AND NEW FORMS OF THE COMPOUND OF FORMULA (I), AND METHODS OF USE THEREOF

PRIORITY OF INVENTION

This application is a National Phase application under 35 U.S.C. §371 of PCT Application PCT/EP2011/071821, filed Dec. 5, 2011, which claims the benefit under 35 U.S.C. §119 (e) from U.S. Provisional Application No. 61/419,567, filed Dec. 3, 2010, which are hereby incorporated by reference in their entirety.

The present invention relates to a novel solid state form of [(5-chlorothiophene-2-ylsulfonylcarbamoyl)-(4-(6-fluoro-7-(methylamino)-2,4-dioxo-1,2-dihydroquinazolin-3(4H)-yl)phenyl)amide, potassium salt, to pharmaceutical compositions comprising, and to processes for making, this novel form. The invention further relates to the use of this novel solid state form and the compositions thereof, alone or in combination with one or more therapeutic agent, in the treatment of various conditions, particularly in the treatment of a condition or a disorder associated with platelet ADP receptor inhibition, in particular, $P2Y_{12}$ inhibition.

The present invention also relates to compositions for the delivery of pharmacologically active agents, to methods of enhancing the bioavailability of pharmacologically active agents, and to methods of treating and/or preventing disease in mammals, particularly humans, by administering a pharmacologically active agent in accordance with the invention.

It is important to provide a compound which is to be developed as a drug (commonly known as a drug substance) in a physical form which can be reliably prepared and purified on a large scale. That physical form should ideally be stable and not degrade on storage. The physical form chosen must also be stable whilst the drug substance is being manufactured as a formulation.

In addition, a given solid state of the drug substance present in a pharmaceutical composition may spontaneously change, thus leading to a change in the efficacy and performance of the pharmaceutical composition which is given to the patient. Whilst developing a pharmaceutical formulation it is therefore important to ensure that the form of the active ingredient does not change during manufacturing or storage of the final dosage forms in the warehouse or pharmacy.

There is thus the need to provide a thermodynamically stable solid form of the drug substance in order to obtain a stable dosage form of the drug substance, as well as a robust process of making the active ingredient and/or the dosage form.

Such a solid state form may also have other desirable characteristics such as low hygroscopicity. For example, a solid form which has a high melting point will be able to withstand higher temperatures than one with a lower melting point. Processing conditions, e.g. drying of the drug substance and/or dosage forms, may then be carried out at a higher temperature, if needed.

It is also the goal of the formulator to develop a dosage form in which the drug substance is readily bio-available, thus enabling the same clinical efficacy to be achieved by the administration of a dosage form with a lower drug dose.

The compound of formula (II), which is also known as elinogrel,

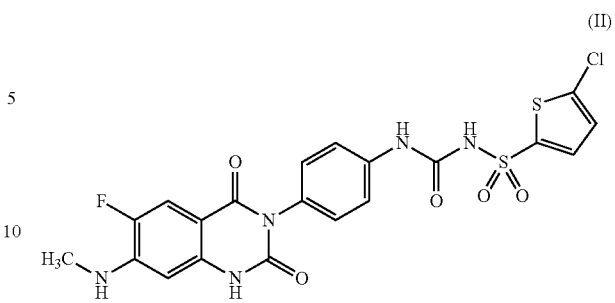

and its potassium salt, the compound of formula (I), having the structural formula

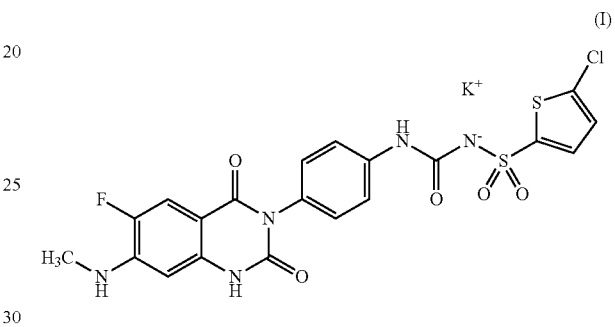

are described as part of a genus of compounds which are platelet ADP receptor inhibitors in WO 07/056,219.

Two crystalline forms of the compound of formula (I) are described in WO 07/056,219. These two crystalline forms, both described as hydrates, were named as Form A and Form B respectively. These hydrate forms suffer from a number of drawbacks, one of which is that they lose their hydrate water at moderate temperatures, lower than 80° C. These hydrate forms of the compound of formula (I) therefore cannot be processed at temperatures higher than 80° C., without losing their polymorphic forms, making these forms less suitable for the formulation of the final dosage forms.

Surprisingly, a solid form of the compound of formula (I), an anhydrous form, which shows desirable characteristics, has been found. This novel solid form is herein referred to as "the anhydrous form of the compound of formula (I)", "the crystalline anhydrous form of the compound of formula (I)", "Form D", "polymorph D", "D", Form poly-D" or alternatively, as "anhydrous form poly-D". Form poly-D is thermodynamically more stable than Form A or B and is surprisingly more easily solubilized in aqueous systems than either Form A or Form B.

Another aspect of the invention pertains to the formulation of a drug substance, in particular, the compound of formula (II), or a pharmaceutically acceptable salt thereof, in a dosage form suitable for administration to the patient. Oral delivery of pharmacologically active agents is generally the delivery route of choice since it is convenient, relatively easy and generally painless, resulting in greater patient compliance relative to other modes of delivery. However, biological, chemical and physical barriers such as poor solubility, varying pH in the gastrointestinal tract, powerful digestive enzymes, and active agent impermeable gastrointestinal membranes, makes oral delivery of some pharmacologically active agents to mammals problematic.

In particular, formulation of the compound of formula (II) has proven difficult due, at least in part, to the poor aqueous solubility of the free acid form which is <0.1 mg/ml (i.e. practically water insoluble) at pH 1.0-7.4. The pKa of the compound of formula (II) is about 3.3, with a log P of about 2.5 and log D (pH7.4) of about −1.6. The second pKa is 10.3.

The compound of formula (II) is a weak acid with poor aqueous solubility at acidic pH<0.1 mg/ml (i.e. practically water insoluble) at pH 1.0-7.4. The aqueous solubility increases at a higher pH (e.g. ≥1 mg/ml at pH 8 or above). In certain instances, the active agent is initially present at least partly in an ionized form. In certain other instances, the active agent is initially present in an un-ionized form.

Techniques have been disclosed for preparing sustained (or controlled) release pharmaceutical formulations of the compound of formula (II), and salts thereof, (see e.g. U.S. patent application Ser. No. 12/618,511 filed Nov. 13, 2009, and WO 2007/056219)

However, there exists a continuing need for further improvement in pharmaceutical preparations with an immediate release (IR) profile which, for example, provide still greater bioavailability of the compound of formula (II). Thus, the present invention provides a dosage form of the compound of formula (II) which exhibits multi-pH dissolution, immediate release and improved pharmacokinetic properties and stability in storage.

In one aspect, the present invention provides the compound, [(5-chlorothiophene-2-ylsulfonylcarbamoyl)-(4-(6-fluoro-7-(methylamino)-2,4-dioxo-1,2-dihydroquinazolin-3 (4H)-yl)phenyl)amide, potassium salt, having the structural formula (I)

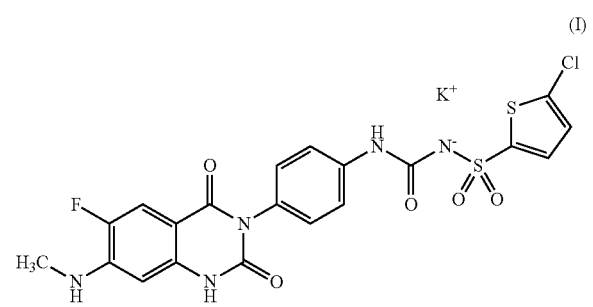 [SMILES: CNc1cc2[nH]c(=O)n(-c3ccc(NC(=O)[N-]S(=O)(=O)c4ccc(Cl)s4)cc3)c(=O)c2cc1F ; [K+]]

in a crystalline anhydrous form.

In another aspect of the invention, there is provided a crystalline anhydrous form of the compound of formula (I) characterized in that said form has at least one of the following characteristics:
(a) an X-ray powder diffraction pattern with peaks at 11.2, 15.8, and 26.4 degrees two theta (±0.2 degree) (CuK$_\alpha$λ=1.54059 Å), or an X-ray powder diffraction pattern substantially in accordance with that shown in FIG. 1;
(b) a differential scanning calorimetry (DSC) melting followed by decomposition with an onset temperature of about 324° C. or a differential scanning calorimetry thermogram (DSC) substantially in accordance with that shown in FIG. 2;
(c) an FT-IR spectrum with the bands at 3427, 1716, 1637, 1514 and 1240 cm$^{-1}$, or a FT-IR spectrum substantially in accordance with that shown in FIG. 3;
(d) an FT-Raman spectrum with the bands at 1216, 1176, 699, 343 and 133 cm$^{-1}$, or a FT-IR spectrum substantially in accordance with that shown in FIG. 4; and
(e) shifts at about 165.7, 152.3, 146.4, 141.2, 130.2, and 112.8 ppm (±0.2 ppm) when characterized by $^{13}$C solid state NMR In another aspect of the invention, there is provided a pharmaceutical composition comprising a compound of the formula (I) in a crystalline anhydrous form, and one or more pharmaceutically acceptable carriers or excipients.

In another aspect of the invention, there is provided a pharmaceutical composition comprising a compound of the formula (I) in a crystalline anhydrous form for use alone or as part of a multi-component treatment regimen for the prevention or treatment of cardiovascular diseases, particularly those related to thrombosis.

In addition, there is provided a process for making a compound of the formula (I) in a crystalline anhydrous form.

Accordingly, the present invention is directed to an orally administrable pharmaceutical composition which, unexpectedly, greatly enhances the bioavailability of a weakly acidic drug compound or a pharmaceutically acceptable salt thereof, with poor aqueous solubility, such as the compound of formula (II). Specifically, the invention provides an orally administrable solid pharmaceutical composition comprising: a) at least about 15% by weight the compound of formula (II), or a pharmaceutically acceptable salt (for example the potassium salt), thereof relative to the total weight of the overall pharmaceutical composition, and b) at least one pharmaceutically acceptable carrier.

In another aspect the present invention provides a solid pharmaceutical composition comprising: a) about 15% to about 90% by weight the compound of formula (II), or a pharmaceutically acceptable salt (for example the potassium salt), thereof relative to the total weight of the overall pharmaceutical composition, and b) at least one pharmaceutically acceptable carrier.

In a further aspect, the invention is directed to a compressed solid dosage form comprising: a) solid pharmaceutical composition comprising: a) at least about 15% the compound of formula (II), or a pharmaceutically acceptable salt (for example the potassium salt), thereof by weight relative to the total weight of the overall pharmaceutical composition, and b) at least one pharmaceutically acceptable carrier.

In a still further aspect, the invention is directed to a method of treating or preventing thrombotic conditions in a mammal in need thereof, which method comprises administering to said mammal an effective amount of a solid pharmaceutical composition comprising: a) at least about 15% by weight the compound of formula (II), or a pharmaceutically acceptable salt (for example the potassium salt), thereof, relative to the total weight of the overall pharmaceutical composition, and b) at least one pharmaceutically acceptable carrier.

In another aspect the present invention provides a method to aid in dissolving the compound of formula (I) or of formula (II), comprising the step of: providing the compound of formula (I) or of formula (II) in a composition with a disintegrant selected from the group consisting of croscarmellose sodium (ACDISOL®), sodium starch glycolate and crospovidone or a crystallization inhibitor selected from the group consisting of a poly(vinylpyrrolidone) and derivatives thereof, cellulosic polymers such as hydroxypropylmethylcellulose (HPMC) and hypromellose acetate succinate, xanthan gums, pectins, alginates, tragacanth and derivatives, gum arabic and derivatives, carrageenans, agar and derivatives, polysaccharides from microbiological sources, arabinogalactanes, galactomannans, dextrans, carboxylic acid and derivatives such as oleic acid, gelatin and surface active agents such as poly (vinylpyrrolidone), poloxamer and sodium lauryl sulfate; in an amount of from at least about 3% by weight relative to the total weight of the overall pharmaceutical composition.

In a further aspect the present invention provides a method of producing a solid pharmaceutical composition comprising the compound of formula (II) or of formula (I); by contacting a) at least about 15% the compound of formula (II) or formula (I) or a pharmaceutically acceptable salt thereof by weight relative to the total weight of the overall pharmaceutical composition, with b) at least one pharmaceutically acceptable carrier, an alkaline excipient and/or a crystallization inhibitor.

Another aspect of the present invention relates to a method for producing a tablet.

Further aspects and embodiments of the disclosure are set forth in the following description and claims.

DETAILED DESCRIPTION

Definitions

Figure 1:
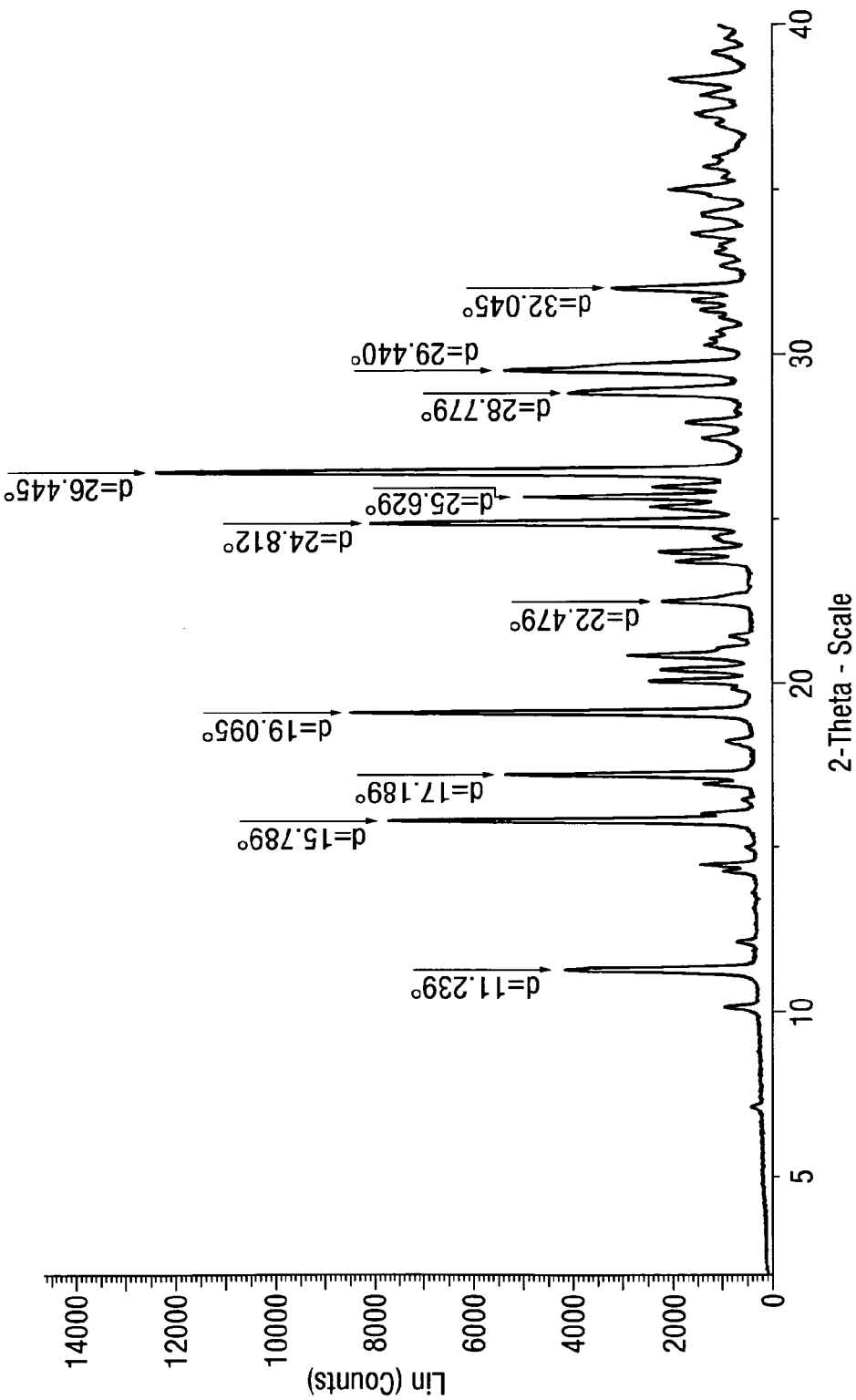
FIG. 1 shows an X-ray powder diffraction pattern of the anhydrous form of the compound of formula (I).

Definitions of various terms which are used herein are listed below.

The term "compound of the invention" refers to the novel solid form of the compound of formula (I), and in particular, a compound of the formula (I) in a crystalline anhydrous form. This term encompasses "the anhydrous form of the compound of formula (I), "Form poly-D" or alternatively, as "anhydrous form poly-D".

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The present invention includes all crystalline and pharmaceutically acceptable isotopically-labelled forms of the compound of formula (I). In an isotopically-labelled form, one or more atoms are replaced by an atom or atoms having the same atomic number, but an atomic mass or mass number different from the atomic mass or mass number which predominates in nature. Suitable isotopes include isotopes of hydrogen, such as $^{2}H$ and $^{3}H$; carbon, such as $^{11}C$, $^{13}C$ and $^{14}C$; nitrogen, such as $^{13}N$ and $^{15}N$; oxygen, such as $^{15}O$, $^{17}O$ and $^{18}O$. Certain isotopically-labelled compounds, such as those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{15}O$ and $^{13}N$, can be useful in Positron Emission Tomography (PET) studies for examining substrate receptor occupancy. Isotopically-labeled compounds can generally be prepared by conventional techniques known to those skilled in the art or by processes analogous to those described in the accompanying Examples and Preparations using an appropriate isotopically-labeled reagent in place of the non-labeled reagent previously employed.

The singular forms "a," "an," and, "the" include plural references unless the context clearly dictates otherwise. Thus, for example, reference to a compound refers to one or more compounds or at least one compound. As such, the terms "a" (or "an"), "one or more", and "at least one" can be used interchangeably herein.

The phrase "about" as used herein is used to provide flexibility to a numerical range endpoint by providing that a given value may be "a little above" or "a little below" the endpoint accounting for variations one might see in measurements taken among different instruments, samples, and sample preparations.

As used throughout the specification and in the claims, the term "treatment" embraces all the different forms or modes of treatment as known to those of the pertinent art and in particular includes preventive, curative, delay of progression and palliative treatment.

The terms "therapeutic agent," "active agent," "active compound," or in some cases "compound," "bioactive agent," "pharmaceutically active agent," and "pharmaceutical," and "drug" are used interchangeably herein to refer to a substance having a pharmaceutical, pharmacological, psychosomatic, or therapeutic effect. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, cocrystals, and salts and solvates of co-crystals, etc. including crystal modifications such as polymorphs and amorphous forms etc. The aforementioned modifications of the pharmacological active agent comprises the solid state and were meaningful also the liquid state.

As used herein, an "effective amount" or a "therapeutically effective amount" of a drug refers to a non-toxic, but sufficient amount of the drug, to achieve therapeutic results in treating a condition. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients.

A "polymer" as used herein refers to a polymer such as cellulose derivatives, dextrans, starches, carbohydrates, base polymers, natural or hydrophilic gums, such as xanthans, alginates, gelatins; polyacrylic acids, polyvinyl alcohol (PVA), polyvinyl pyrrolidone (PVP), carbomers, combinations thereof or the like.

As used herein, the term "immediate release" as applied to drug formulations have the meanings ascribed to them in "Remington's Pharmaceutical Sciences," 18.sup.th Ed., p. 1677, Mack Pub. Co., Easton, Pa. (1990).

Unless specified otherwise, a range of "molecular weight" of a polymer (e.g., hydroxypropyl methylcellulose (HPMC) or polyvinyl pyrrolidone (PVP) or a gelation facilitator agent (e.g., a polyethylene glycol) described below is a weighted average molecular weight (measured by gel permeation chromatography).

The term "disintegration" refers to the disintegration of tablets or capsules into their constituent granules or particles when placed in a liquid medium in the experimental condition. Complete disintegration is defined as that state in which any residue of the unit, except fragments of insoluble coating or capsule shell, remaining on the screen of the test apparatus is a soft mass having no palpably firm core. Disintegration does not imply complete solution of the unit or even of its active constituent. Suitable methods known in the art for determining the disintegration time of a solid dosage form include, e.g., the USP disintegration test <701>. The term "non disintegrating" refers to a composition that does not fully disintegrate in an hour or less in a suitable aqueous medium determined using the USP disintegration test <701>. The term "slow disintegrating" refers to a composition that fully disintegrates in about an hour to about 30 minutes in a suitable aqueous medium determined using the USP disintegration test <701>.

The term "bioavailability" refers to the rate and/or extent to which a drug is absorbed or becomes available to the treatment site in the body.

In a further aspect of the invention, there is provided a substantially pure form of the compound of the formula (I) in a crystalline anhydrous form.

In another aspect, there is also provided a compound of the formula (I) in a crystalline anhydrous form in 99, 95, 90, 85, 80, 75, 70, or 65% purity.

The present invention also provides a process for the preparation of the compound of formula (I) in crystalline Form poly-D comprising the steps of:

(a) adding, at a temperature between 20-30° C., an aqueous solution of a base, containing between 2.1 and 2.5 molar equivalents of a base, to a suspension of the acid of formula (II)

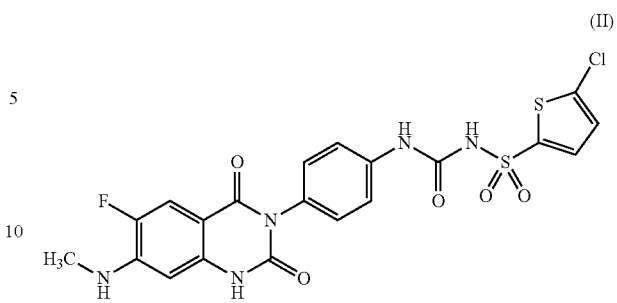

in water, wherein the suspension is initially at a temperature between 20-30° C.; and wherein the base has a pKa of at least 12;
(b) heating the resulting solution to a temperature between 40-50° C.;
(c) filtering the resulting solution at a temperature between 40-50° C.;
(d) adding, at a temperature between 40-50° C., methanol or a 50-90% v/v methanol/water mixture to form a supersaturated solution;
(e) adding, over a period of at least two hours, an aqueous acidic solution, containing 1 molar equivalent less than the amount of base used in step (a), to the supersaturated solution, wherein the acid has a pKa in the range of 3-6; wherein the temperature is kept at a temperature between 40-50° C.;
(f) cooling the resulting suspension from a temperature in the range of 40-50° C. to a temperature in the range of 20-30° C. over a period of at least 1.5 hours;
(g) separating and washing the crystals obtained at the end of step (f); and
(g) optionally drying the crystals.

The base which is added in step (a) is used to form the dianion of the acid of formula (II) and has a pKa of at least 12. A suitable base may be selected from KOH, calcium hydroxide, NaOH, L-arginine, and betaine.

The acid which is added in step (e) has a pKa in the range of 3-6 and may be selected from adipic acid, gluconic acid, glutamic acid, lactic acid, palmitic acid, stearic acid and succinic acid.

Drying of the crystals may be carried out by any conventional methods known in the art such as vacuum drying, or convective drying. Drying may be carried out at a temperature between 50-120° C.

In another aspect, the present invention provides a process for the preparation of the compound of formula (I) in crystalline Form poly-D comprising the steps of:
(a') adding, at a temperature between 20-30° C., an aqueous solution of a base, containing between 1.0 and 1.1 molar equivalents of a base, to a suspension of the acid of formula (II)

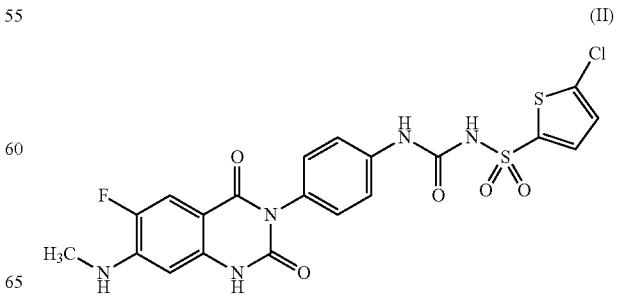

in methanol or a methanol:water mixture, wherein the methanol:water mixture contains at least 50% methanol, wherein the suspension is initially at a temperature between 20-30° C.; and wherein the base has a pKa of at least 5;
(b') heating the resulting mixture to a temperature between 50-60° C.;
(c') filtering the resulting mixture at a temperature between 40-50° C.;
(d') cooling the filtrate from a temperature in the range of 40-50° C. to a temperature in the range of 10 to −10° C. over a period of at least 2 hours;
(e') separating and washing the crystals obtained at the end of step (e'); and
(f') optionally drying the crystals.

The base which is added in step (a') is used to form the mono-anion of the acid of formula (II) and has a pKa of at least 5;

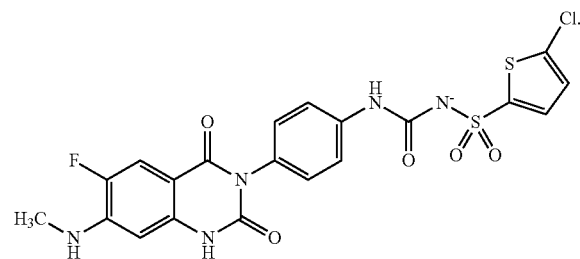 [SMILES: CNc1cc2[nH]c(=O)n(-c3ccc(NC(=O)[N-]S(=O)(=O)c4ccc(Cl)s4)cc3)c(=O)c2cc1F]

A suitable base may be selected from KOH, calcium hydroxide, NaOH, L-arginine, betaine, magnesium hydroxide, choline, diethylamine, lysine, aqueous ammonia, deanol, N-methyl-glucamine). The base may be added as a 5-50% KOH solution.

Optional purification of the resulting mixture, which is obtained after step (b'), may be carried out by adding activated charcoal and stirring the mixture at a temperature between 50-60° C., for at least 30 minutes;

Drying of the crystals may be carried out by any conventional methods known in the art such as vacuum drying, or convective drying. Drying may be carried out at a temperature between 50-120° C.

Administration and Pharmaceutical Compositions

As used herein, the terms "administration," and "administering" refer to the manner in which an active agent is presented to a subject. While much of the disclosure is focused on oral administration, administration can be accomplished by other various art-known routes such as parenteral, transdermal, inhalation, implantation, ocular, otic, etc.

The term "oral administration" represents any method of administration in which an active agent can be administered through the oral route by swallowing, chewing, or sucking an oral dosage form. Such solid or liquid oral dosage forms are traditionally intended to substantially release and or deliver the active agent in the gastrointestinal tract beyond the mouth and/or buccal cavity. Examples of solid dosage forms include conventional tablets, capsules, caplets, etc.

As used herein, "oral dosage form" refers to a formulation that is prepared for administration to a subject through the oral route of administration. Examples of known oral dosage forms, include without limitation, tablets, capsules, caplets, powders, pellets, granules, solutions, suspensions, solution pre-concentrates, emulsions and emulsion pre-concentrates, etc. In some aspects, powders, pellets, granules and tablets may be coated with a suitable polymer or a conventional coating material to achieve, for example, greater stability in the gastrointestinal tract, or to achieve the desired rate of release. Moreover, capsules containing a powder, pellets or granules may be further coated. Tablets may be scored to facilitate division of dosing. Alternatively, the dosage forms of the present invention may be unit dosage forms wherein the dosage form is intended to deliver one therapeutic dose per administration.

In one embodiment, the invention provides a solid pharmaceutical composition comprising: a) at least about 15% by weight the compound of formula (II), or a pharmaceutically acceptable salt (for example the potassium salt), thereof relative to the total weight of the overall pharmaceutical composition, and b) at least one pharmaceutically acceptable carrier.

In another embodiment the present invention provides a solid pharmaceutical composition comprising: a) about 15% to about 90% by weight the compound of formula (II), or a pharmaceutically acceptable salt (for example the potassium salt), thereof relative to the total weight of the overall pharmaceutical composition, and b) at least one pharmaceutically acceptable carrier.

In a further embodiment, the invention is directed to a compressed solid dosage form comprising: a) solid pharmaceutical composition comprising: a) at least about 15% the compound of formula (II), or a pharmaceutically acceptable salt (for example the potassium salt), thereof by weight relative to the total weight of the overall pharmaceutical composition, and b) at least one pharmaceutically acceptable carrier.

In a still further embodiment, the invention is directed to a method of treating or preventing a thrombotic condition in a mammal in need thereof, which method comprises administering to said mammal an effective amount of a solid pharmaceutical composition comprising: a) at least about 15% by weight the compound of formula (II), or a pharmaceutically acceptable salt (for example the potassium salt), thereof relative to the total weight of the overall pharmaceutical composition, and b) at least one pharmaceutically acceptable carrier.

In another embodiment the present invention provides a method to aid in dissolving the compound of formula (II), comprising the step of: providing the compound of formula (II) or a pharmaceutical acceptable salt thereof in a composition with a disintegrant selected from the group consisting of croscarmellose sodium (ACDISOL®), sodium starch glycolate and crospovidone and/or a crystallization inhibitor selected from the group consisting of a poly(vinylpyrrolidone) and a hydroxypropylmethylcellulose in an amount of from at least about 3% by weight relative to the total weight of the overall pharmaceutical composition.

In a further embodiment the present invention provides a method of producing a solid pharmaceutical composition comprising the compound of formula (II) or a pharmaceutical acceptable salt thereof, by contacting a) at least about 15% the compound of formula (II), or a pharmaceutically acceptable salt (for example the potassium salt), thereof by weight relative to the total weight of the overall pharmaceutical composition, with b) at least one pharmaceutically acceptable carrier, an alkaline excipient and/or a crystallization inhibitor.

Another aspect of the present invention relates to a method for producing a tablet.

The composition provides a desired release profile for the active agent, specifically, in multi-stage dissolution method which mimics the gradual pH change in physiological conditions. The dosage forms of the present invention give faster and more complete release in pH 5.0-7.4 stages (after initial exposure to acid environment) compared against conventional immediate release formulations.

The active agent can be in any suitable form. In certain embodiments, the active agent can be in the form of an amorphous solid, a crystal, a granule, or a pellet using the drug in solid or liquid state. These active agent forms may facilitate certain coating processes of the active agents. Moreover, the particle can comprise a single active agent crystal (or granule or pellets or amorphous solid) or can comprise a plurality of active agent crystals (or granules or pellets or amorphous solid), or mixtures thereof.

In yet another embodiment, an active agent is a drug that is unstable if it is in contact with simulated gastric fluid or a gel-forming matrix for a prolonged period of time at low pH (e.g., sensitive to low pH microenvironment).

In the embodiments of the invention, the active agent can be in any suitable form. For example, it can be in the form of a powder, pellet, or a granule (i.e., an aggregate of smaller units of active agent). The active agent can be used and combined with other excipients without using any size enlargement process. An active agent can be pelletized or granulated using any suitable methods known in the art. Pelletization by extrusion (followed by spheronization) or granulation (wet or dry) is commonly defined as a size-enlargement process in which small particles are gathered into larger aggregates in which the original particles can still be identified.

Any suitable granulation methods can be used to produce particles comprising an active agent. By definition, granulation is any process of size enlargement and densification whereby small particles are gathered together into larger, aggregates to render them into a free-flowing state. For example, either wet granulation or dry granulation methods can be used.

Dry granulation refers to the granulation of a formulation without the use of heat and solvent. Dry granulation technology generally includes slugging or roller compaction. Slugging consists of dry-blending, compressing the formulation into a loose, porous tablet (or slug) on a compression machine and subsequently milling it to yield the granules. Roller compaction is similar to slugging, but two counter rotating rollers are used instead of the tableting machines to form compact in the form of a ribbon for milling. See, e.g., *Handbook of Pharmaceutical Granulation Technology*, D. M. Parikh, eds., Marcel-Dekker, Inc. pages 102-103 (1997). Dry granulation technique is useful in certain instances, e.g., when the active agent is sensitive to heat, water or solvent. Alternatively, the active agents are granulated with high shear mixer granulation ("HSG") or fluid-bed granulation ("FBG"). Both of these granulation processes provide enlarged granules but differ in the apparatti used and the mechanism of the process operation. Blending and wet massing by HSG is accomplished by an impeller and a chopper in the mixer. Mixing, densification, and agglomeration of wetted materials are achieved through shearing and compaction forces exerted by the impeller. The wet mass is dried using commercial equipment such as a tray drier or a fluid-bed drier. On the other hand, fluidization is the operation by which a mass of powder is manipulated to exhibit fluid-like characteristics using a gas or air at high velocity as the fluidization vehicle. Such a fluidized bed resembles a vigorously boiling fluid, with solid particles undergoing turbulent motion, which can be generally increased with gas velocity. FBG is then a process by which granules are produced by spraying and drying a binder solution onto a fluidized powder bed to form larger granules in a fluidbed dryer. The binder solution can be sprayed from, e.g., one or more spray guns positioned at any suitable manner (e.g., top or bottom). The spray position and the rate of spray may depend on the nature of the active agent and the binder(s) used, and are readily determinable by those skilled in the art.

Optionally, granulated active agents can be milled after wet granulation or drying. Milling can be performed using any commercially available equipment, e.g., COMIL® equipped with a screen having a suitable mesh size. The mesh size for the screen of a COMIL® can be selected depending on the size of the active agent granule or pellet desired. Typically, the mesh size can range from 0.331 inch screen (mesh 20) to 0.006 inch screen (mesh 100). The milling process aids in providing relatively uniform granule size. After the wet granulated active agents are milled, they may be further dried (e.g., in a fluidbed drier) if desired. Typically, the mean size of the active granule can range from about 20 μm to about 3 mm, optionally about 50 μm to about 2 mm, about 100 μm to about 1 mm. Typically, the bulk density and the tap density of the active agent granules range from about 0.1 g/ml to about 1.5 g/ml, optionally about 0.3 to about 0.8 g/ml, optionally about 0.4 g/ml to about 0.6 g/ml. Bulk density is measured based on USP method (see US testing method <616>).

Other Components and Dosage Forms

The compositions of the present invention may take the form of an immediate release tablets, pills, capsules, or the like. Preferably, the dosage form is an immediate-release tablet.

Dosage forms such as dissolving tablets, containing at least about 15% by weight the compound of formula (II), or a pharmaceutically acceptable salt (for example the potassium salt), and a pharmaceutically acceptable carrier, such as an alkalizer, a disintegrant, a crystallization inhibitor and combinations thereof described herein, offer advantages over other traditional formulations for oral administration. For example, in multi-stage dissolution method, these dosage forms gave faster and more complete release in pH 5.0-7.4 stages (after initial exposure to acid environment) compared against conventional immediate release formulations. Similarly, the bioavailability of the therapeutic agent is increased, thereby reducing the time to onset of therapeutic activity as compared to traditional dosage forms for oral administration.

In addition, the preferred dosage forms of the present invention (e.g., at least about 15% by weight the compound of formula (II), or a pharmaceutically acceptable salt (for example the potassium salt), thereof and optionally containing at least one carrier such as an alkalizer, a disintegrant, a crystallization inhibitor and combinations thereof described herein) offer advantages over dosage forms using lesser amounts of active ingredient. Importantly, the larger dosage forms of the present invention help for a faster release of the active in a hydrated media. The bioavailability of the therapeutic agent is increased, and the time to onset of therapeutic activity is modulated as compared to dosage forms for oral administration that do not contain the above mentioned functional excipients in any combination and the same drug dose.

As used herein, the term "dosage form" refers to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. In other embodiments, a tablet dosage form of the present invention can be prepared according to the procedures set forth, for example, in *Remington: The Science and Practice of Pharmacy*, 20$^{th}$ Ed., Lippincott, Williams & Wilkins (2003); *Pharmaceutical Dosage Forms, Volume 1: Tablets*, 2$^{nd}$ Ed., Marcel Dekker, Inc., New York, N.Y. (1989); and similar publications. The dosage form to be administered will, in any event, contain a quantity of the therapeutic agent in a therapeutically effective amount for relief of the condition being treated when administered in accordance with the teachings of this invention.

Typically, the tablet compositions of the present invention comprise at least about 15.0% by weight of the active agent (in whatever chosen form, measured as per its free acid form), and typically from about 15.0% to about 90.0% and more typically from about 30.0% to 50.0%. In some embodiments, about 35.0% by weight of the active agent is used. One skilled in the art understands that the foregoing percentages will vary depending upon the particular source of active agent utilized, the amount of active agent desired in the final formulation, as well as on the particular release rate of active agent desired.

The compositions of the present invention can additionally include a carrier. In one group of embodiments the composition of the present invention comprises an alkalizer, a crystallization inhibitor, a disintegrating agent, or a combination thereof.

Alkalizers

Formulations were designed to provide an alkaline microenvironment for these compounds. The alkalizer is used to create a microenvironment in the formulation to optimize drug release after the formulation is in a hydrated media. The alkalizers of the compositions described herein are capable of raising the pH of the micro-environment for these compounds in the hydrated formulation to a pH greater than about the pKa1 of the active acid, irrespective of the starting pH of the media. In one embodiment, the alkalizers of the compositions described herein are capable of raising the pH of the micro-environment in the hydrated formulation to typically about 9.0-9.5, irrespective of the starting pH of media. In this way, the alkalizer helps increase the solubility of the active as pH increases up to pH 10 in a hydrated media to enhance the product release/dissolution profile from the hydrated formulation. Although pH adjusting agents may be used with the alkalizers of the present invention, one skilled in the art will appreciate that acidic agents can also be used to adjust the pH of the alkalizer as long as the alkalizer as a whole raises the pH of the micro-environment for these compounds in the hydrated formulation to greater than about the pKa1 of the active acid (pKa about 3.3).

In one embodiment and as described in more detail below, the alkalizer of the compositions described herein helps to increase the solubility of the active agent as pH increases up to pH 10 in a hydrated media to enhance the product release profile. In another embodiment, the alkalizer of the compositions described herein helps to maintain substantially the entire active agent in its dissolved ionized form in the formulation when it is in a hydrated media.

Suitable alkalizer agents include, but are not limited to, organic and inorganic basic compounds of a wide range of aqueous solubilities and molecular weights and the like and mixtures thereof. Representative examples of bases are found in Table 1 below. Representative examples of inorganic basic salts include ammonium hydroxide, aluminum hydroxide, alkali metal salts, alkaline earth metal salts such as magnesium oxide, magnesium hydroxide, calcium hydroxide, sodium hydroxide, potassium hydroxide, potassium carbonate, sodium bicarbonate and the like and mixtures thereof. In one aspect, the invention provides a solid composition wherein the alkalizer selected from the group consisting of calcium carbonate, magnesium oxide, calcium hydrogen phosphate. The solubility and the molecular size of the alkalizer may affect its diffusion rate in the hydrated product and influence the dissolution profile of the active agent.

In one aspect, the invention provides a solid composition wherein the amount of alkalizer is from about 3 to about 90% and more specific between 3 and 50% and even more specific between 3 and 35% weight percent of the total composition. In one aspect, the invention provides a solid composition wherein the combined weight percent of the alkalizer is greater than or equal to the weight percent of the active.

In one aspect, the invention provides a solid composition, wherein the composition provides at least about 15% release of the active between about 15 to about 30 minutes following administration or use.

In one embodiment, the alkalizers of the present invention are binary alkalizers, for example comprising a carbonate salt or a bicarbonate salt and a second alkalizer, for example magnesium oxide. The concentration of each alkalizer component is tailored such that the final pH of the micro-environment for these compounds in the hydrated formulation is achieved and sustained for a period of time, e.g., for at least about an hour. Selection of an appropriate weight ratio for each alkalizer component can be easily determined to achieve the dissolution profile in an aqueous environment. For example, the weight ratio of carbonate salt to bicarbonate salt can be from about 1:10 to about 10:1, preferably from about 1:5 to about 5:1, more preferably from about 1:3 to about 3:1, and still more preferably from about 1:2 to about 2:1

Suitable carbonate salts and bicarbonate salts are described above. The amount of carbonate salt or bicarbonate salt used in the binary alkalizer is an amount that is sufficient, when used with the second alkalizer to raise pH of the micro-environment for these compounds in the hydrated formulation to a pH of about the pKa of the active ingredient or more, preferably about 8.5 or more, and more preferably about 9 or more (e.g., about 9-11), irrespective of the starting pH. In certain instances, the amount of the second alkalizer in the binary alkalizer is greater than or equal to the amount of the carbonate salt or bicarbonate salt. For example, the weight ratio of the second alkalizer to the carbonate salt or bicarbonate salt can be from about 1:1 to about 10:1, preferably from about 1:1 to about 5:1, and more preferably from about 1:1 to about 3:1. In certain other instances, the amount of the second alkalizer in the binary alkalizer is less than or equal to the amount of the carbonate salt or bicarbonate salt. For example, the weight ratio of the second alkalizer to the carbonate salt or bicarbonate salt can be from about 1:1 to about 1:10, preferably from about 1:1 to about 1:5, and more preferably from about 1:1 to about 1:3.

The second alkalizer is generally selected from a metal oxide such as magnesium oxide or aluminum oxide; a phosphate salt such as monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate. In addition other alkaline excipients can be used such as listed in Table 1.

TABLE 1

Alkaline Excipients

| Alkaline excipient | Aqueous Solubility mg/ml | Material state | Tm ° C. | MW | CAS No. |
|---|---|---|---|---|---|
| Meglumine | 1000 | solid | 128 | 195 | 6284-40-8 |
| Eglumine. | | solid | 138 | 209 | 14216-22-9 |
| Ca2CO3 | insoluble | solid | 825 | 100 | 471-34-1 |
| MgO | very slightly soluble | solid | 2800 | 40 | 1309-48-4 |
| CaHPO4 2H2O | insoluble | solid | | 172 | 7789-77-7 |
| Na2HPO4 xH2O | very soluble | solid | | 142 | 7558-79-4 |

TABLE 1-continued

Alkaline Excipients

| Alkaline excipient | Aqueous Solubility mg/ml | Material state | Tm ° C. | MW | CAS No. |
|---|---|---|---|---|---|
| NaH2PO4 xH2O | 1000 | solid | | 120 | 7558-80-7 |
| KH2PO4 | 20% free sol | | | 136 | 7778-77-0 |
| K2HPO4 | >50% | | | | |
| Arginin | 150 | solid | 244 | 174 | |
| Benzathine | | | | 240 | |
| Lysine | free soluble | solid | 210 | 146 | |
| Epolamine | | | | 115 | |
| Tromethamine | 550 | solid | 171 | 121 | |
| Zn(OH)2 | | | | 99 | |

However, one skilled in the art will appreciate that any metal oxide or salt of citric acid, phosphoric acid, boric acid, ascorbic acid, or acetic acid is suitable for use in the alkalizers of the present invention. The amount of the second alkalizer used in the binary alkalizer is an amount that is sufficient, when used with the carbonate salt or bicarbonate salt, to raise the pH of the micro-environment for these compounds in the hydrated formulation to a pH of about the pKa of the active acid or more. Typically this is about 9.0 to about 9.5 irrespective of the starting pH. Preferably about 8.5 or more, and more preferably about 9 or more (e.g., about 9-11), irrespective of the starting pH. In some embodiments, a metal oxide such as magnesium oxide or aluminum oxide is the preferred second alkalizer. In a particularly preferred embodiment, the metal oxide is amorphous magnesium oxide.

Alternatively, in still yet another embodiment, the alkalizers of the present invention are ternary alkalizers comprising a carbonate salt, a bicarbonate salt, and a third alkalizer. Suitable carbonate salts and bicarbonate salts are described above. The amount of carbonate salt and bicarbonate salt used in the ternary alkalizer is an amount that is sufficient, when used with the third alkalizer, to raise the pH of the micro-environment for these compounds in the hydrated formulation to a pH of about the pKa of the active acid or more, preferably about 8.5 or more, and more preferably about 9 or more (e.g., about 9-11), irrespective of the starting pH.

In one group of embodiments, the alkalizer is selected from the group consisting of magnesium oxide, calcium carbonate, calcium phosphate and combinations thereof. In another group of embodiments, the alkalizer is calcium carbonate. In another group of embodiments, the alkalizer is magnesium oxide. In another group of embodiments, the alkalizer is present in an amount of about 8% to about 40% by weight. In another group of embodiments, the alkalizer is present in an amount of about 11% by weight.

Crystallization Inhibitors

One issue in using solubility enhancers with low solubility drugs is the crystallization of the drug in gastro-intestinal fluid. Therefore, in one group of embodiments, the composition of the present invention also includes a crystallization inhibitor. As used herein, the term "crystallization inhibitor" refers to salts, ions, carbohydrates, surfactants, amino acids, polymers and other compounds which, when present in solution, decrease the crystallization of the compound of formula (II), or a pharmaceutically acceptable salt thereof, especially when measured as described in Example 13: Super-saturation measurements and stabilization. Examples of crystallization inhibitors include, but are not limited to polyvinyl pyrrolidone, for example those products known under the registered trade marks PVP K30, PVP K29/32 and PVPP XL (crosslinked PVP), in particular having a molecular weight in excess of 1 000 000, more particularly having a particle size distribution of less than 400 microns or less than 74 microns. Another example is HPMC (hydroxypropyl methyl cellulose) that are known under the trade mark Pharmacoat e.g. Pharmacoat 603.

It should be noted that crystallization inhibitors may act as stabilizing or solubilizing agents. Stabilizing agents preserve the unit activity of the compound of formula (II) in storage and may act by preventing formation of aggregates, or by preventing degradation of the compound of formula (II) molecule, or a pharmaceutically acceptable salt thereof, (e.g. by acid catalyzed reactions). Solubilizers are mainly alkaline excipients or polymers that inhibit to a certain extend the precipitation of the drug in solution. Solubilizing agents or solubilizers increase the solubility of the compound of formula (II) above 0.1 mg/mL. Solubilizers may raise the concentrations of the compound of formula (II), or a pharmaceutically acceptable salt thereof, above 0.2 mg/mL or above 1 mg/mL. In one group of embodiments, compositions include the solubilizer excipient(s) or a mixture of such excipients in a ratio of 1:10 to 10:1 (drug:excipient(s)). In another group of embodiments, the crystallization inhibitor is selected from the group consisting of a poly(vinylpyrrolidone) and a hydroxypropylmethylcellulose. In another group of embodiments, the hydroxypropylmethylcellulose has a viscosity of about 5 cP. In another group of embodiments, the poly(vinylpyrrolidone) is PVP K30. In another group of embodiments, the crystallization inhibitor is present in an amount of from at least about 3% by weight relative to the total weight of the overall pharmaceutical composition. In another group of embodiments, the crystallization inhibitor is present in an amount from at least 3% to about 50% by weight relative to the total weight of the overall pharmaceutical composition. In another group of embodiments, the crystallization inhibitor is present in an amount from 3-10%, e.g. 4.22%, by weight of the dosage form.

Disintegrants

Where accelerated release is desired, e.g. about 20% release within 30 minutes, more particularly within 15 minutes period, a disintegrant such as croscarmellose sodium (AcDiSiol), sodium starch glycolate and crospovidone, may be used. It is also possible to use reactive additives (effervescent mixtures) that effect rapid disintegration of the tablet in the presence of water; for example so-called effervescent tablets that contain an acid in solid form, typically citric acid, which acts in water on a base containing chemically combined carbon dioxide, for example sodium hydrogencarbonate or sodium carbonate, and releases carbon dioxide. Thus in one group of embodiments, the disintegrant is selected from the group consisting of croscarmellose, sodium starch glycolate and crospovidone. In another group of embodiments, the disintegrant is a croscarmellose. In another group of embodiments, the disintegrant is croscarmellose sodium. In another group of embodiments, the disintegrant is present in an amount from at least about 2.5% by weight relative to the total weight of the overall pharmaceutical composition. In another group of embodiments, the disintegrant is present in an amount from at least about 2.5% to about 11% by weight relative to the total weight of the overall pharmaceutical composition.

Other Carriers

As used herein, the term "carrier" also refers to a typically inert substance used as a "diluent" or vehicle for a drug such as a therapeutic agent. The term also encompasses a typically inert substance that imparts cohesive qualities to the composition. Suitable carriers for use in the compositions of the present invention include, without limitation, a binder, a gum base, and combinations thereof. Non-limiting examples of carriers and diluents include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. These diluents can be pre-processed to improve their flowability and taste by methods known in the art such as freeze drying (see, e.g., Fundamentals of Freeze-Drying, *Pharm. Biotechnol.*, 14:281-360 (2002); Lyophililization of Unit Dose Pharmaceutical Dosage Forms, *Drug. Dev. Ind. Pharm.*, 29:595-602 (2003)); solid-solution preparation (see, e.g., U.S. Pat. No. 6,264,987); and lubricant dusting and wet-granulation preparation with a suitable lubricating agent (see, e.g., *Remington: The Science and* Practice of Pharmacy, supra). For example, Mannogem® and Sorbogem®, sold by SPI Pharma Group (New Castle, Del.), are freeze-dried processed forms of mannitol and sorbitol, respectively. Typically, the compositions of the present invention comprise from about 25% to about 90% by weight of the diluents, and preferably from about 50% to about 80%. However, one skilled in the art will appreciate that the compositions of the present invention can be made without any diluents, e.g., to produce a highly friable dosage form.

In one aspect, the invention provides a solid composition comprising a diluent selected from the group consisting of microcrystalline cellulose, lactose and mannitol.

The formulation further may comprise pH adjusting agents; antioxidants, such as butylated hydroxytoluene and butylated hydroxyanisole; plasticizers; glidants; protecting agents; elastomeric solvents; bulking agents; wetting agents; emulsifying agents; solubilizing agents; lubricants; suspending agents; preserving agents such as methyl-, ethyl-, and propyl-hydroxy-benzoates; sweetening agents; flavoring agents; coloring agents; and disintegrating agents.

It is preferred to add such pH-adjusting acids to create and regulate a buffered microenvironment when combined with one or more alkalizers to obtain the desired delivery rate for the drug agent. Among those agents are but not limited to citric-acid, succinic acid, tartaric acid, acetic acid, and vitamin C. Preferred are buffer substances like citric acid. The pharmaceutical formulations disclosed herein can further comprise antioxidants and chelating agents. For example, the pharmaceutical formulations can comprise butylated hydroxyanisole (BHA), butylated hydroxytoluene (BHT), propyl gallate (PG), sodium metabisulfite, ascorbyl palmitate, potassium metabisulfite, disodium EDTA (ethylenediamine tetraacetic acid; also known as disodium edentate), EDTA, tartaric acid, citric acid, citric acid monohydrate, and sodium sulfite. In one embodiment, the foregoing compounds are included in the pharmaceutical formulations in amounts in the range of about 0.01% to about 5% w/w. In one specific embodiment, the pharmaceutical formulation includes BHA, BHT, or PG used at a range of about 0.02% to about 1% and disodium EDTA, citric acid, or citric acid monohydrate used at a range of about 2% to about 5%. In a preferred embodiment, the pharmaceutical formulation includes BHA used at about 0.05% w/w.

Lubricants can be used to prevent adhesion of the dosage form to the surface of the rollers, dies and punches, and to reduce inter-particle friction. Lubricants may also facilitate ejection of the dosage form from the die cavity and improve the rate of granulation flow during processing. Examples of suitable lubricants include, without limitation, magnesium stearate, glyceryl behenate, calcium stearate, zinc stearate, stearic acid, silicon dioxide, talc, polyethylene glycol, mineral oil, carnauba wax, palmitic acid, sodium stearyl fumarate sodium laurel sulfate, glyceryl palmitostearate, myristic acid and hydrogenated vegetable oils and fats, as well as other known lubricants, and/or mixtures of two or more thereof. In one embodiment, the lubricant, if present, of the stock granulation is magnesium stearate. The compositions of the present invention can comprise from about 0% to about 10% by weight of the lubricant, and preferably from about 0.25% to about 5%.

In another embodiment, the composition can also optionally include an anti-adherent or glidant. Examples of glidants and/or anti-adherents suitable for use herein include but are not limited to, silicon dioxide, colloidal silicon dioxide, magnesium silicate, magnesium trisilicate, talc, and other forms of silicon dioxide, such as aggregated silicates and hydrated silica, or mixtures. In another embodiment, the composition can also optionally include an opacifying agent, such as titanium dioxide, for example. In yet another embodiment, the composition can also optionally include one or more colorants, for example, iron oxide based colorant(s).

The tablet composition may further comprise a protecting agent. The protecting agent coats at least part of the therapeutic agent, typically upon the mixing of the two agents. The protecting agent may be mixed with the therapeutic agent in a ratio from about 0.1 to about 100 by weight, preferably in a ratio from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered in the stomach within about 7 to about 12 hours, preferably within about 12 hours. Materials suitable as protecting agents may be used alone or in combination in the tablet compositions of the present invention.

The tablet composition may also comprise one or more elastomeric solvents such as rosins and resins. Non-limiting examples of such solvents may be used alone or in combination in the tablet compositions of the present invention. In addition, the tablet composition may further comprise waxes such as beeswax and microcrystalline wax, fats or oils such as soybean and cottonseed oil, and combinations thereof. Moreover, the tablet composition may additionally include plasticizers such as softeners or emulsifiers. Such plasticizers may, for example, help reduce the viscosity of the gastric solution of the dissolved tablet to a desirable consistency and improve its overall texture and bite and help facilitate the release of the therapeutic agent. Non-limiting examples of such plasticizers may be used alone or in combination in the tablet compositions of the present invention.

In one embodiment of the stock granulation, the bulking agent is microcrystalline cellulose and/or lactose monohydrate, the binder, if present, is pregelatinized starch, the disintegrant, if present, is sodium starch glycolate, croscarmellose sodium, crospovidone, or combinations thereof; the lubricant, if present, is magnesium stearate and the glidant and/or anti-adherent, if present, is colloidal silicon dioxide and/or talc.

Sweetening agents can be used to improve the palatability of the composition by masking any unpleasant tastes it may have. Examples of suitable natural or artificial sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Hydrogenated starch hydrolysate, and the potassium, calcium, and sodium salts of 3,6-dihydro-6-methyl-1,2,3-oxathiazin-4-one-2,2-dioxide may also be used. The compositions of the present invention can comprise from about 0% to about 80% by weight of the sweetening agent, preferably from about 0.5% to about 75%, and more preferably from about 0.5% to about 50%.

Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g., white, milk, dark), vanilla, caramel, coffee, hazelnut, combinations thereof, and the like. Coloring agents can be used to color code the composition, for example, to indicate the type and dosage of the therapeutic agent therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present invention can comprise from about 0% to about 10% by weight of the flavoring and/or coloring agent, preferably from about 0.1% to about 5%, and more preferably from about 2% to about 3%.

Preparation of Solid Compositions Comprising Active Agent into Tablets

Any suitable methods can be used to mix the formulation comprising the active agent. In one embodiment, the active agent and carrier are combined, mixed and the mixture may be directly compressed into a tablet. Typically, one or more vehicles or additives may be added to the mixture to improve flow and compressible characteristics. These additives include, for example, lubricants, such as magnesium stearate, zinc stearate, stearic acid, talc, and the like; flavors; and sweeteners. Compression, e.g. direct compression, has advantages, such as reducing cost, time, operational pace, and machinery; preventing active agent-excipient interaction; and less instability of active agent. Direct blending or dry granulation can also eliminate the possible pollution by organic solvent.

In another embodiment, some of the formulation components may be partially granulated prior to compression or all of the formulation components may be granulated prior to compression. For example, the active agent, alone can also be granulated prior to mixing. Any suitable granulation methods can be used to mix the formulation. In one embodiment, a wet granulation process can be used to mix one or more components of the formulation. For example, high shear granulation or fluid-bed granulation processes can be used. Any suitable commercially available granulation equipment can be used in these processes. After the granulation of one or more components of the formulation, optionally, granulated formulation can be milled. Milling can be performed using any suitable commercially available apparatus, e.g., COMIL® equipped with a screen of a suitable mesh size. The mesh size for the screen of a COMIL® can be selected depending on the size of the granules desired. After wet granulated active agents are milled, they may be further dried (e.g., in a fluid-bed) if desired.

After preparing the formulation as described above, the formulation is compressed into a tablet form. This tablet shaping can be done by any suitable means, with or without compressive force. For example, compression of the formulation after the granulation step or blending can be accomplished using any tablet press, provided that the tablet composition is adequately lubricated unless an external lubrication process is used. The level of lubricant in the formulation is typically in the range of 0.5-2.0%, e.g. with magnesium stearate which is most commonly used as a lubricant. Many alternative means to effectuate this step are available, and the invention is not limited by the use of any particular equipment. The compression step can be carried out using a rotary type tablet press. The rotary type tableting machine has a rotary turret with multiple stations of dies and punches. The formulation is fed into the die and is subsequently compressed.

The tablet compositions can have any desired shape, size, and texture. The diameter and shape of the tablet depends on the molds, dies, and punches selected for the shaping or compression of the granulation composition. For example, tablets can be discoid, oval, oblong, round, cylindrical, triangular, and can have the shape of a stick, tab, pellet, sphere, and the like. Similarly, the tablet can be any desirable color. For example, the tablet can be any shade of red, blue, green, orange, yellow, violet, indigo, and mixtures thereof, and can be color coded to indicate the type and dosage of the therapeutic agent therein. The tablets may be scored to facilitate breaking. The top or lower surface can be embossed or debossed with a symbol or letters. The tablets can be individually wrapped or grouped together in pieces for packaging by methods well known in the art.

The compression force can be selected based on the type/model of press, what physical properties are desired for the tablets product (e.g., desired hardness, friability, etc.), the desired tablet appearance and size, and the like. Typically, the compression force applied is such that the compressed tablets have a hardness of at least about 2 kP. These tablets generally provide sufficient hardness and strength to be packaged, shipped or handled by the user. If desired, a higher compression force can be applied to the tablet to increase the tablet hardness. However, the compression force is preferably selected so that it does not cause capping or lamination of tablets. Preferably, the compression force applied is such that the compressed tablet has a hardness of less than about 250 kN.

Typically, the final tablet will have a weight of about 50 mg to about 2000 mg, more typically about 100 mg to about 1000 mg, or about 150 mg to about 500 mg. In one aspect, the invention provides a solid composition wherein the amount of active agent is about 150 mg. In one aspect, the invention provides a solid composition wherein the amount of active agent is about 100 mg. In one aspect, the invention provides a solid composition wherein the amount of active agent is about 75 mg. In one aspect, the invention provides a solid composition wherein the amount of active agent is about 60 mg. In one aspect, the invention provides a solid composition wherein the amount of active agent is about 50 mg. In one aspect, the invention provides a solid composition wherein the amount of active agent is about 40 mg. In one aspect, the invention provides a solid composition wherein the amount of active agent is about 30 mg. In one aspect, the invention provides a solid composition wherein the amount of active agent is about 25 mg. In one aspect, the invention provides a solid composition wherein the amount of active agent is about 20 mg.

If desired, other modifications can be incorporated into embodiments of the invention. For example, modification of drug release through the tablet matrix of the present invention can also be achieved by any known technique, such as, e.g., application of various coatings, e.g., ion exchange complexes with, e.g., Amberlite IRP-69.

Capsules may be prepared by filling the blend along with suitable excipients into gelatin capsules, using a suitable filling machine.

The pharmaceutical formulations of the invention can be packaged in any packaging that facilitates stability of the drug formulation. For example, sealed high density polyethylene (HDPE) bottles containing silica gel desiccant or aluminum blister lined with PVC (thermoform PVC blister) or aluminum-aluminum blister can be used. Use of such packaging helps to control unwanted oxidation and moisture ingress of the product. Preferably, the ingredients in the pharmaceutical compositions of the instant invention are homogeneously or uniformly mixed throughout the solid dosage form. Whether the active agents are distributed randomly or non-randomly, a tablet can comprise one or more types of active agent, and/or one or more types of coating materials. The non-random distribution of active agent can be represented quantitatively by different amounts in different layers or qualitatively by having different forms of active agent in different layers, e.g., as having more coating materials in the particle in the outer layers as compared to the inner layers of the tablet, or, vice versa.

The formulations presented in the examples 3 and 4 are well within typical limits for film-coated tablets especially in-process controls and dissolution at pH 7.4 (see Example 5) and stability (see Example 6).

The film-coated tablets exhibit a high dissolution in the multi pH dissolution test (Table 13, Table 14) that prove a good in vivo dissolution and this tablets compensating the very poor solubility of the drug substance (see saturation solubility in Example 9) thereby provide evidence that the used excipients like disintegrant, alkalizer and crystallization inhibitor enhance the dissolution of the drug substance.

Surprisingly the extremely high supersaturation of this drug has been found and subsequently is being used for a tablet formulation by testing pharmaceutical excipients in a non-obvious way to find materials that perform a strong crystallization inhibition of this drug (as described in detail in Example 11).

Methods of Administration

The compositions of the present invention are useful in therapeutic applications, e.g., for treating thrombosis. Importantly, the compositions of the present invention provide the rapid and predictable delivery of an active agent with surprisingly low inter-subject variability in terms of maximum plasma concentration ($C_{max}$) and the time to reach the maximum plasma concentration ($T_{max}$) by modulating the pH around the active. In particular, the delivery of the therapeutic agent optimizes absorption. As a result, the therapeutic agent can reach the systemic circulation in a substantially shorter period of time and at a substantially higher concentration than with traditional oral (e.g., tablet) administration. In addition, the compositions of the present invention offer advantages over compositions for oral administration that do not contain a carrier (e.g. alkalizer, disintegrant, crystallization inhibitor or combination thereof) described herein. In particular, because the alkalizer, disintegrant, crystallization inhibitor or combination thereof in the compositions of the present invention can help increase the solubility of the active as pH increases up to pH 10 and/or prevent crystallization in a hydrated media to enhance the product release profile, the therapeutic agent reaches the systemic circulation in a substantially shorter period of time (e.g., reducing the time to onset of therapeutic activity) and at a substantially higher concentration than with compositions for oral administration that do not contain the carrier.

The compositions of the present invention have particular utility in the area of human and veterinary therapeutics. The compositions of the present invention may be administered to deliver an active agent to any animal in need thereof, including, but not limited to, mammals, such as rodents, cows, pigs, dogs, cats, and primates, particularly humans. Generally, administered dosages will be effective to deliver picomolar to micromolar concentrations of the active agent to the appropriate site. Administration of the compositions of the present invention is preferably carried out via any of the accepted modes of oral administration.

The following examples are intended for illustration only, are not intended to limit the scope of the invention. The contents of all U.S. patents and other references cited in this application are hereby incorporated by reference in the entirety.

Accordingly, the present invention provides a pharmaceutical composition as described herein for use as a medicament. A pharmaceutical composition as described herein is also provided for use in the treatment of a disorder or a condition associated with platelet ADP receptor inhibition, in particular, $P2Y_{12}$ inhibition.

A pharmaceutical composition as described therein for the manufacture of a medicament for the treatment of a disorder or a condition associated with platelet ADP receptor inhibition, in particular, $P2Y_{12}$ inhibition.

A method of preventing or treating a disorder or a condition associated with platelet ADP receptor inhibition, in particular, $P2Y_{12}$ inhibition, comprising administrating a therapeutically effective amount of the composition to a subject in need of such a treatment is also provided.

Therapeutic Use

The present invention also provides a method for treating or preventing a condition or a disorder associated with platelet ADP receptor inhibition, in particular, $P2Y_{12}$ inhibition, which method comprises administering a therapeutically effective amount of the compound of the invention, or a pharmaceutical composition of the invention, to a subject in need thereof.

The present invention also provides a method for treating or preventing a condition or a disorder associated with platelet ADP receptor inhibition, in particular, $P2Y_{12}$ inhibition, which method comprises administering a therapeutically effective amount of the pharmaceutical composition of the invention to a subject in need thereof.

The present invention also provides a method for treating or preventing a condition or a disorder associated with platelet ADP receptor inhibition, in particular, $P2Y_{12}$ inhibition, which method comprises administering a therapeutically effective amount of the pharmaceutical composition of the invention, wherein the pharmaceutical composition comprises a compound of the invention, to a subject in need thereof.

Thus the present invention provides the use of a compound of the invention, alone or in combination with another therapeutic agent for the manufacture of a medicament for treating or preventing a condition or a disorder associated with platelet ADP receptor inhibition, in particular, $P2Y_{12}$ inhibition, in animals, particularly humans. A compound of the invention, alone or in combination with another therapeutic agent is also provided for use in treating or preventing a condition or a disorder associated with platelet ADP receptor inhibition, in particular, $P2Y_{12}$ inhibition, in animals, particularly humans.

A pharmaceutical composition of the invention is also provided for use in treating or preventing a condition or a disorder associated with platelet ADP receptor inhibition, in particular, $P2Y_{12}$ inhibition, in animals, particularly humans.

A pharmaceutical composition of the invention, wherein the pharmaceutical composition comprises a compound of the invention, is also provided for use in treating or preventing a condition or a disorder associated with platelet ADP receptor inhibition, in particular, $P2Y_{12}$ inhibition, in animals, particularly humans.

The pharmaceutical compositions of the present invention are suitable for use alone or as part of a multi-component treatment regimen for the prevention or treatment of cardiovascular diseases, particularly those related to thrombosis. For example, a compound or pharmaceutical composition administered in accordance with the present the invention may be used as a drug dosage regimen for any thrombosis, particularly a platelet-dependent thrombotic indication, including, but not limited to, acute coronary syndrome, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses, and hypercoagulable states related to genetic predisposition or cancers. In other groups of embodiments, the indication is selected from the group consisting of percutaneous coronary intervention (PCI) including angioplasty and/or stent, acute myocardial infarction (AMI), unstable angina (USA), coronary artery disease (CAD), transient ischemic attacks (TIA), stroke, peripheral vascular disease (PVD), Surgeries-coronary bypass, carotid endarectomy.

The pharmaceutical composition can also be used in chronic coronary heart disease and in secondary prevention of the above listed cardiovascular diseases.

[The pharmaceutical compositions may also be used as part of a multi-component treatment regimen in combination with other therapeutic or diagnostic agents in the prevention or treatment of thrombosis in a mammal. In certain preferred embodiments, compounds or pharmaceutical compositions used the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, enoxaparin, glycoprotein (GP) 2b/3a inhibitors, aspirin, statins, angiotensin-converting enzyme (ACE) inhibitors or warfarin or anti-inflammatories (non-steriodal anti-inflammatories, cyclooxygenase II inhibitors). Co-administration may also allow for application of reduced doses of both the anti-platelet and the thrombolytic agents and therefore minimize potential hemorrhagic side-effects. Compounds and pharmaceutical compositions used in the invention may also act in a synergistic fashion to prevent reocclusion following a successful thrombolytic therapy and/or reduce the time to reperfusion.

In one embodiment, the pharmaceutical compositions of the present invention are used alone or in combination with aspirin. The aspirin may be used in an amount of 10-300 mg per day, or 70-120 mg per day. In one embodiment, the aspirin is used in an amount of 81 mg per day.

EXAMPLES

General

Commonly used pharmaceutical excipients may be used in the general formulations. Microcrystalline cellulose, Lactose Fastflo may be used alone or in combination as a diluent in the formulations. Talc may be used as a glidant and magnesium stearate may be as a lubricant in the formulations. Water and non-water soluble solubility enhancers including PVP and HPMC may be used also. In addition suitable disintegrants, e.g. Ac-Di-Sol® or crospovidone (PVPP), may be used to ensure rapid disintegration.

Since polymorphs B and A are moisture sensitive, a wet granulation process cannot be used to prepare formulations involving these solid forms. However, since polymorph poly-D has a low moisture sensitivity, it is possible to prepare a formulation using a wet granulation process.

The packaging format used for packaging the core tablets for both formulations are 75 cc round white HDPE bottles with desiccant (2 gm per bottle) and child resistant closure with induction seal. Several different formulations are made for a 30-150 mg Immediate Release (IR) capsule or tablet with a weight of up to about 450 to about 650 mg. The declared dosing strengths refer to the free acid quantity of Elinogrel, e.g. Film-coated tablet 75 mg. The value of the % w/w concerning the composition of the dosage form (in the Tables below) refer to the % w/w of the potassium salt depicted as the compound of formula (I) including—if meanigful—crystal water. The details of the formulations are summarized in the following tables.

Example 1

Process of Making the Compound of Formula (I) in Crystalline Form Poly-D 1 equivalent of the acid of formula (II) is suspended in water, then 2.35 equivalents of a 50% w (50% weight KOH/weight solution) KOH solution are added. The resulting mixture is simultaneously heated to 50° C. Methanol is then added at 40-50° C. to form a supersaturated solution. 1.35-1.55 equivalents of 5-30% acetic acid is then added slowly during a period of approximately 2-12 hours. The resulting suspension is cooled to 20° C. in approximately 1.5-10 hours. The crystals are filtered and washed, first with methanol: water (mixture 3:7) and then with pure methanol. Drying is performed at 60-80° C., or under vacuum at temperatures between 60 and 120° C.

Example 2

Alternative Procedure for Making Polymorph Poly-D 1.0-1.1 equivalent of KOH as a 5-50% w (5-50% weight KOH/weight solution) KOH solution (titrated) is added to a suspension of 1.0 equivalent of the compound of formula (II) in methanol/water (1:1 w/w). The resulting suspension is heated to 50-60° C. for an hour. After dissolution of the free acid, the turbid solution (impurities are not dissolved) is treated with charcoal and subsequently filtered over a heated (50° C.) membrane filter into a vessel kept at 45° C.

The suspension is cooled to −10° C. in 9 h and continuously stirred at this temperature for at least 2 hours.

The slurry is filtered and washed with a cold methanol/water mixture (1/1 w/w) and pure methanol at room temperature. Drying is performed at 60-120° C. and <20 mbar (>12 hours) until the methanol content is <0.2%.

Example 3

Analytical Characterization of the Compound of Formula (I) in Crystalline Form Poly-D X-Ray Powder Diffraction Pattern The X-ray powder pattern was recorded on a Bruker D8 Advance Diffractometer using $CuK_\alpha$ radiation with a wavelength of 1.54059 A, scan rate (continuous scan): 0.3 s/step, stepsize: 0.017° (2Theta), scan range 2°-4¹° (2Theta). Temperature: ambient (20° C. to 25° C.).

As will be appreciated by the skilled person, the relative intensities of the various peaks within the Tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Tables. The skilled person will also appreciate that measurements using a different wavelength will result in different shifts according to the Bragg equation $-n\lambda = 2d \sin \theta$. Such alternative PXRD patterns generated by use of alternative wavelengths are nevertheless representations of the same material.

The XRPD profiles for the solid form are shown in FIG. 1. The list of characteristic peaks are listed herein in the Table below.

| deg (2-theta) (±0.2 degree) | d-values (Å) | relative intensity |
|---|---|---|
| 11.2 | 7.87 | medium |
| 15.8 | 5.61 | medium |
| 17.2 | 5.15 | medium |
| 19.1 | 4.64 | medium |
| 22.5 | 3.95 | weak |
| 24.8 | 3.59 | medium |
| 25.6 | 3.47 | medium |
| 26.4 | 3.37 | strong |
| 28.8 | 3.10 | medium |
| 29.4 | 3.03 | medium |
| 32.0 | 2.79 | medium |

The most significant diffraction peaks are 11.2°, 15.8° and 26.4° (±0.2 degree) (2-theta)

Differential Scanning Calorimetry (DSC) of the Compound of Formula (I) in Crystalline Form Poly-D.

Figure 2:
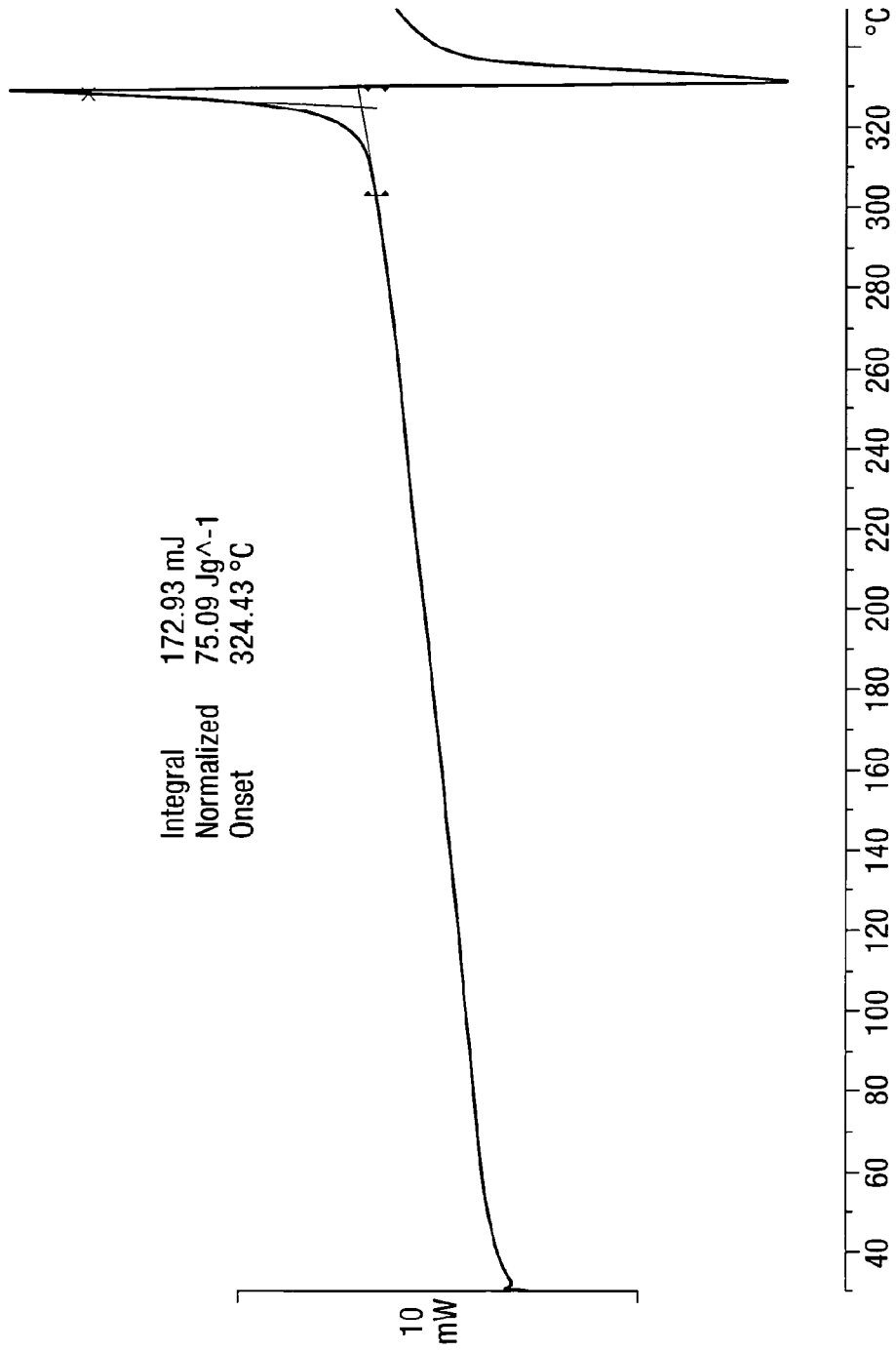
FIG. 2 shows the DSC curve of the anhydrous form of the compound of formula (I).

The Differential Scanning calorimetry curve (DSC) (see FIG. 2) was recorded on a Mettler DSC822e using a heating rate of 10K/min, a crucible with pin hole and a sample mass of 1-3 mg.

The anhydrous form poly-D shows a melting followed by decomposition with an onset temperature of about 324° C. when heated in a DSC at 10K/min in sample pan with a pin hole.

FT-IR Spectrum of the Compound of Formula (I) in Crystalline Form Poly-D.

Figure 3:
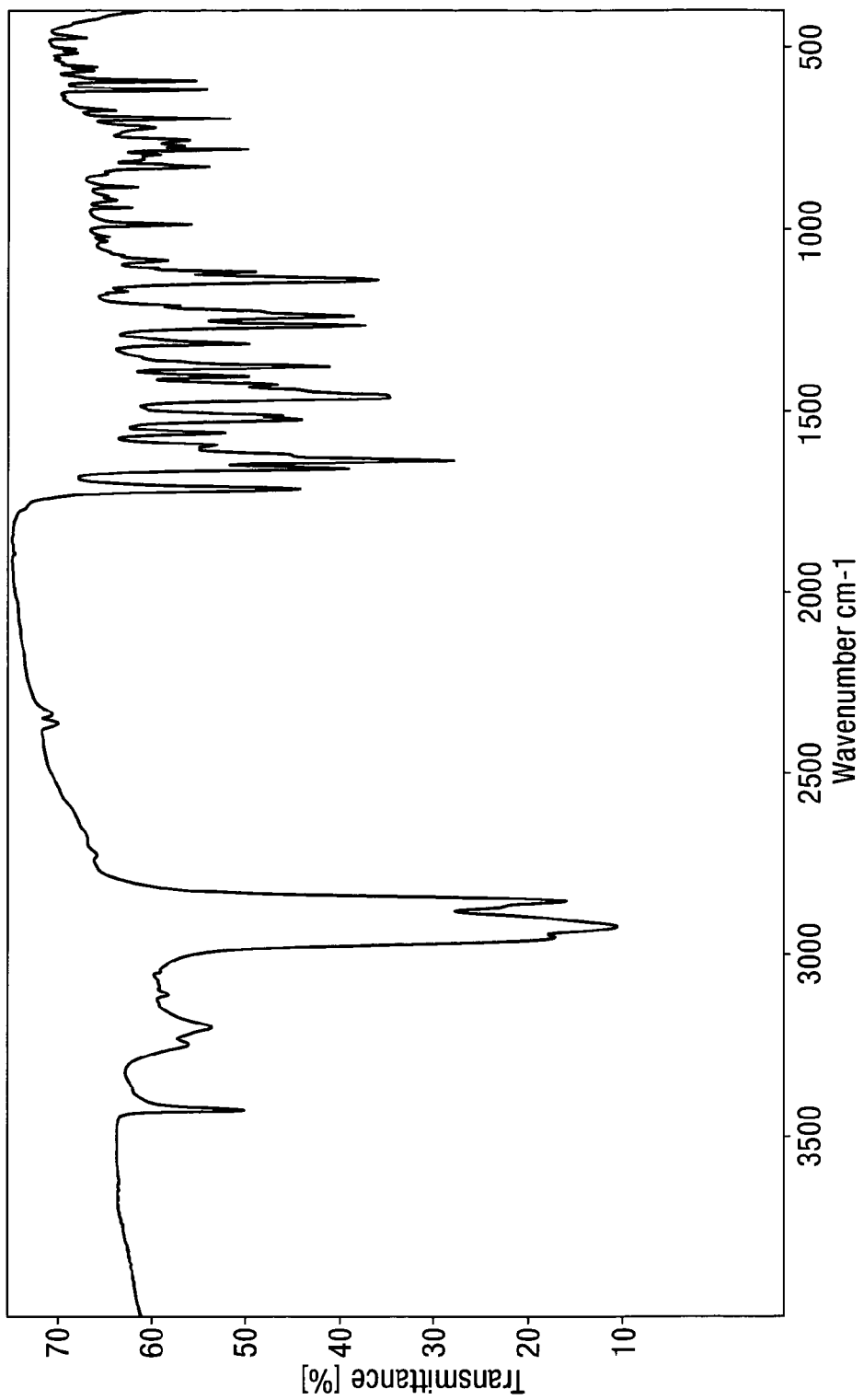
FIG. 3 shows the FT-IR spectrum of the anhydrous form of the compound of formula (I).

The FT-IR spectrum (FIG. 3) was recorded on a Bruker Vertex 70 FT-IT spectrophotometer in Nujol.

Significant FT-IR bands of the anhydrous form poly-D of the compound of formula (I) are as follows (with most characteristic bands highlighted in bold):
3427, 3247, 3200, 1716, 1637, 1560, 1514, 1463, 1379, 1317, 1240, 1142, 782, 618 $cm^{-1}$ FT-Raman Spectrum of the Compound of Formula (I) in Crystalline Form Poly-D.

Figure 4:
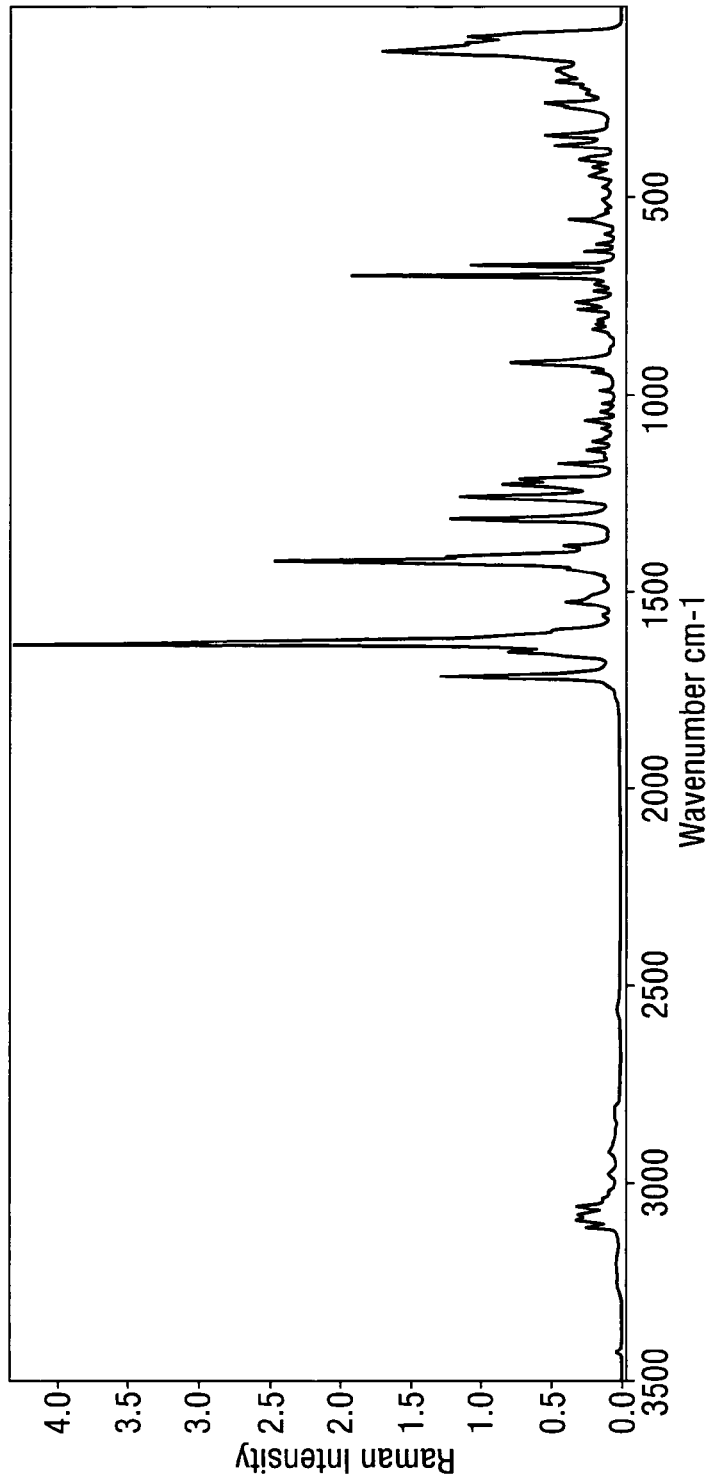
FIG. 4 shows the FT-Raman spectrum of the anhydrous form of the compound of formula (I).

The FT-Raman spectrum (FIG. 4) was recorded on a Bruker RFS100 spectrophotometer. List of significant FT-Raman bands of the anhydrous form poly-D of the compound of formula (I) (with most significant bands highlighted in bold):
1715, 1632, 1421, 1313, 1216, 1176, 919, 699, 343 and 133 $cm^{-1}$ Solid State NMR of the Compound of Formula (I) in Crystalline Form Poly-D.

Figure 5:
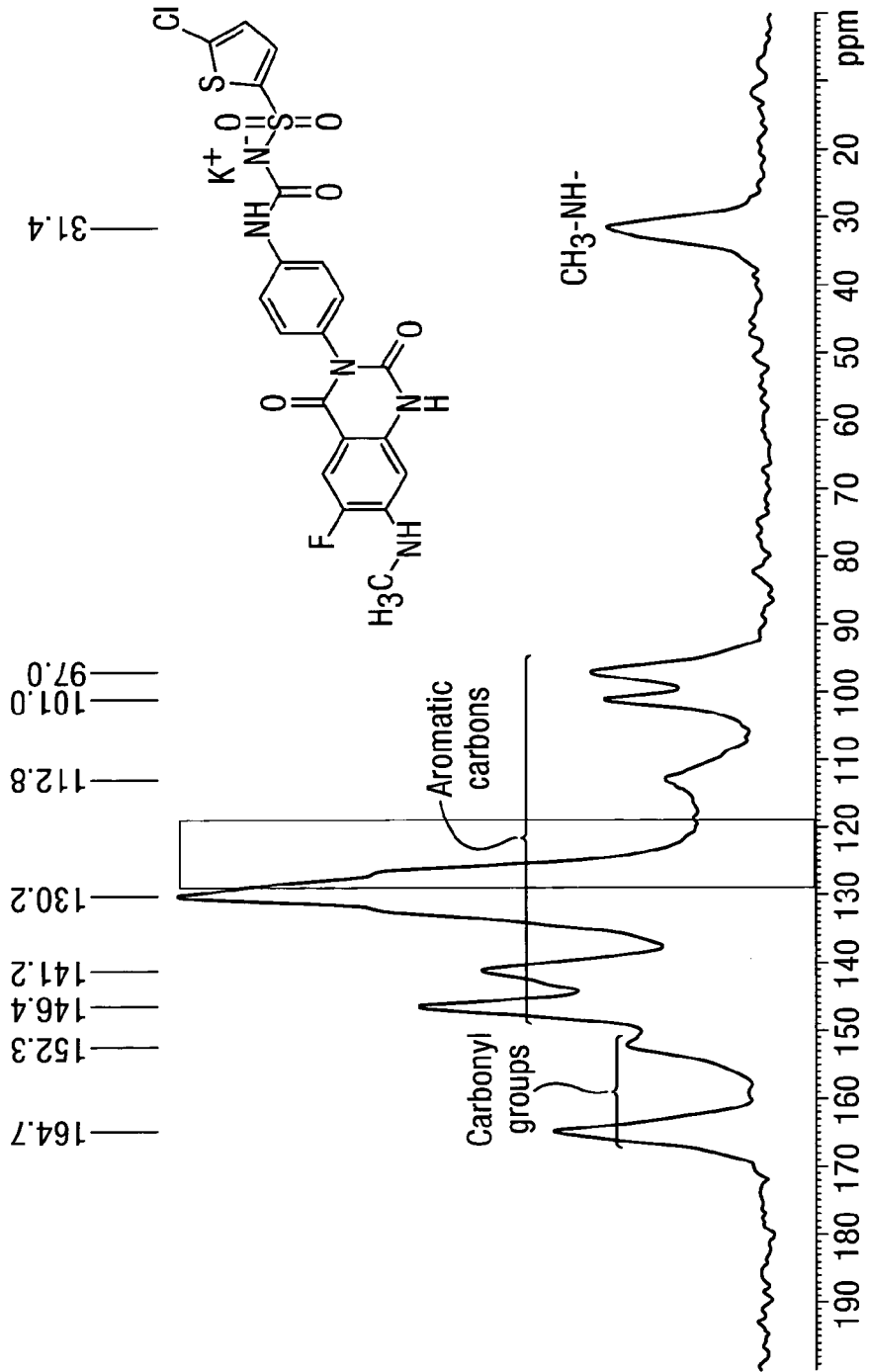
FIG. 5 shows the solid state NMR spectrum of the anhydrous form of the compound of formula (I).
Figure 6:
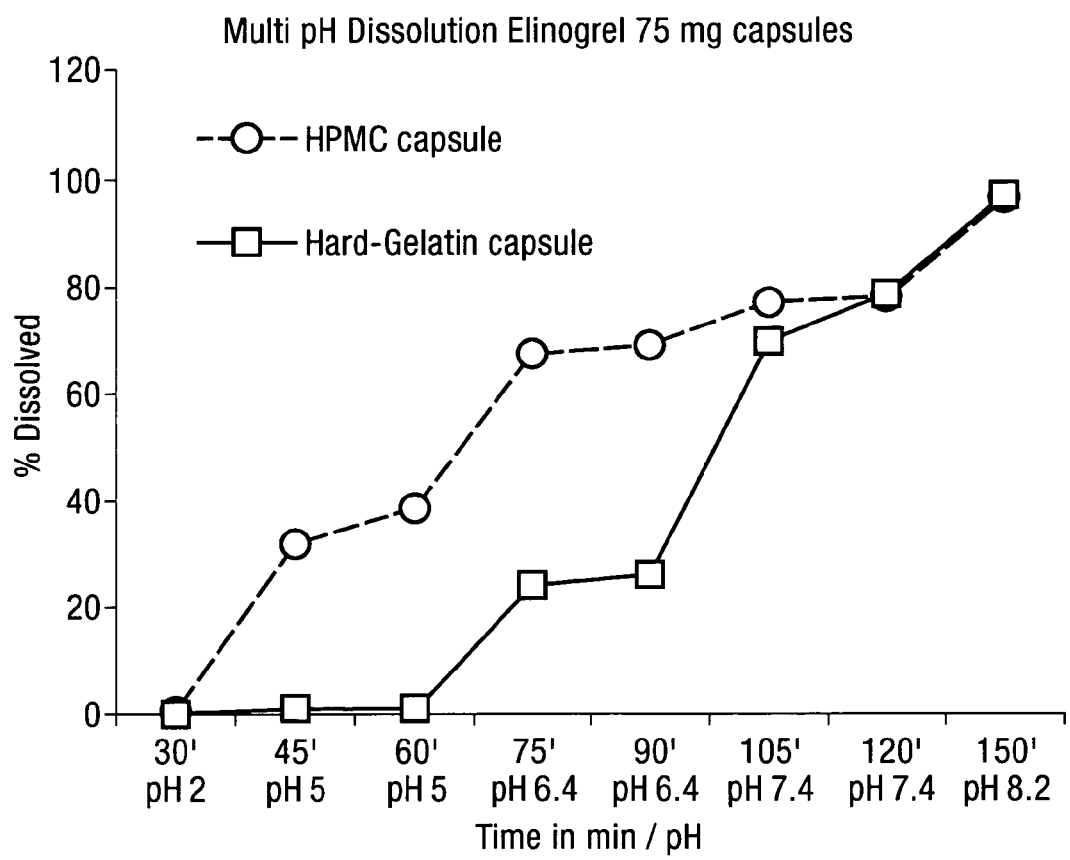
FIG. 6 shows multi-pH dissolution profiles for Example 5. The five pH stage dissolution method includes pH 2.0 buffer at 15, 30 min; pH 5.0 buffer at 45, 60 min; pH 6.4 buffer at 75, 90 min; pH 7.4 buffer at 105, 120 min; pH 8.2 buffer at 150 minutes of dissolution evaluation.

The $^{13}C$ CP/MAS solid state NMR spectrum (FIG. 5) was recorded on a Bruker ASX300 NMR spectrometer using spin rates of about 4000 Hz, 90° proton pulse length of 4 µs, contact times of 1 ms and delay times of about 1 s.

List of Significant Chemical Shifts of Form Poly-D:
165.7, 152.3, 146.4, 141.2, 130.2, 112.8, 101.0, 97.0, and 31.4 (±0.2) ppm Single Crystal Structure of the Compound of Formula (I) in Crystalline Form Poly-D The crystal structure of the anhydrous form poly-D was solved by single crystal X-ray analysis of using high-energy X-ray radiation and is characterized by the following crystal parameters:

| | |
|---|---|
| Empirical formula | $C_{20}H_{14}ClFKN_5O_5S_2$ |
| Formula weight | 562.03 |
| Temperature | 100(2) K |
| Wavelength | 0.71073 Å |
| Crystal system | Monoclinic |
| Space group | P21/c |
| Unit cell dimensions | a = 7.249(14) Å   $\alpha = 90°$. |
| | b = 17.42(4) Å   $\beta = 95.73(3)°$. |
| | c = 17.63(4) Å   $\gamma = 90°$. |
| Volume | 2216(8) Å3 |
| Z | 4 |
| Density (calculated) | 1.684 Mg/m3 |

The crystal structure analysis confirms the new form poly-D of the compound of formula (I) is an anhydrous crystal form.

Example 4

Relative Thermodynamic Stability of the Anhdrous Form Poly-D

The relative thermodynamic stability of the anhydrous form poly-D in comparison with the known Forms A and B of the compound of formula (I) was assessed by cross-seeding experiments, where mixtures of the anhydrous form poly-D and Form A and mixtures of the anhydrous form poly-D and Form B were separately suspended in water, an organic solvent or mixtures of water and organic solvents. The suspension was then equilibrated at various temperatures for several days. The solid parts were then isolated by filtration and analysed by X-ray powder diffraction. The results show that Form A and Form B convert into the anhydrous form poly-D, thus indicating that Anhydrous form poly-D is thermodynamically stable in respect to Form A or Form B of the compound of formula (I).

|  | 25° C./4 days | | 50° C./3 days | |
| --- | --- | --- | --- | --- |
|  | Form poly-D | Form A/poly-D (1:1) | Poly-D | Form A/poly-D (1:1) |
| water | No change | No change | No change | Poly-D |
| MeOH/water 1:2 v/v | No change | Poly-D | No change | Poly-D |
| MeOH/water 1:1 v/v | No change | Poly-D | No change | Poly-D |
| MeOH/water 2:1 v/v | No change | Poly-D | No change | Poly-D |
| MeOH | No change | Poly-D | No change | Poly-D |

|  | 1:1 Form B:Poly-D mixture 25° C./1 day |
| --- | --- |
| water | No change |
| MeOH/water 1:2 v/v | Poly-D |
| MeOH/water 1:1 v/v | Poly-D |
| MeOH/water 2:1 v/v | Poly-D |
| MeOH | Poly-D |

Example 5

50 mg of the Compound of Formula (I) in Immediate Release Capsule (Reference Formulation)

TABLE 2

Composition The compound of formula (I) 50 mg immediate release capsule

| Ingredient | Function | % w/w |
| --- | --- | --- |
| The compound of formula (I) (Form B) | Active | 12.5 |
| Mannitol | Filler | 84.5 |
| Talc | Glidant | 2.0 |
| Magnesium stearate | Lubricant | 1.0 |

Preparation

The composition (Form B) is prepared by weighing and mixing the compound of formula (I) and excipients except magnesium stearate. The mixture is sieved and mixed and sieved magnesium stearate is added. The composition is blended, dry granulated by roller compaction and milling and then filled into capsules.

Example 6

75 mg of the Compound of Formula (I-Immediate Release Hydroxypropylmethyl Cellulose (HPMC) Capsule (Reference Formulation)

TABLE 3

Composition 75 mg of the compound of formula (I)-immediate release hydroxypropylmethyl cellulose (HPMC) capsule

| Ingredient | Function | % w/w |
| --- | --- | --- |
| The compound of formula (I) (Form B) | Active | 21.41 |
| Mannitol DC | Filler | 75.64 |
| Talc PH | Glidant | 1.97 |
| Magnesium steareate (external phase) | Lubricant | 0.98 |

Preparation

The composition is prepared by weighing and mixing the compound of formula (I) (Form B) and excipients except magnesium stearate. The mixture is sieved and mixed and sieved magnesium stearate is added. The mixture is blended and dry granulated by roller compaction and milling and then filled into capsules.

Example 7

30 mg FMI Tablet:30 mg of the Compound of Formula (I)-Film Coated Tablet (FCT)

TABLE 4

Composition 30 mg FMI tablet, 30 mg of the compound of formula (I)-film coated tablet

| Ingredient | Function | % w/w |
| --- | --- | --- |
| The compound of formula (I) (Form poly-D) | Active | 33.53 |
| PVP K30 | Crystallization inhibitor | 4.17 |
| Magnesium oxide | Alkalizer | 11.25 |
| Destab Calcium Carbonate 90S ultra | Alkalizer | 28.13 |
| PVPP XL | Disintegrant | 5.42 |
| Cellulose MK GR | Filler | 12.08 |
| Aerosil 200 PH | Glidant | 0.43 |
| Magnesium Stearate (External phase) | Lubricant | 0.84 |
| Tablet core weight |  | 92 mg |

HPMC Coating (Basic lacquer composition form Colorcon Ldt, UK, known as Opadry):

TABLE 5

Composition HPMC Coating 30 mg of the compound of formula (I) film coated tablet (FCT)

| Ingredient | % w/w |
| --- | --- |
| Basic coat White | 2.79 |
| Basic coat Yellow | 1.10 |
| Basic coat Red | 0.25 |
| Basic coat Black | 0.02 |
| Coat weight | 14 mg |

Preparation

The composition is prepared by weighing and mixing the compound of formula (I) (Form poly-D) and excipients except half of the magnesium stearate and Aerosil. The mixture is sieved and mixed and sieved magnesium stearate is added. The composition is blended and dry granulated by roller compaction. The granules are blended with the Aerosil and subsequently with the remaining magnesium stearate and this final mixture is compressed into tablets. The tablets are dedusted and subsequently coated with HPMC containing lacquer in a coating pan. The batch size is about 8.28 kg. The in-process controls are as follows (target values):

TABLE 6

In-process control results

| Control | Range | unit |
| --- | --- | --- |
| Tablet press compression force | 9.5 | kN |
| Tablet size | 6 round | mm |

Example 8

75 mg FMI: 75 mg of the Compound of Formula (I)-Film Coated Tablet

TABLE 7

Composition 75 mg FMI-75 mg of the compound of formula (I)-film coated tablet

| Ingredient | Function | % w/w |
| --- | --- | --- |
| The compound of formula (I) (Form poly-D) | Active | 33.82 |
| PVP K30 | Crystallization inhibitor | 4.20 |
| Magnesium oxide | Alkalizer | 11.34 |
| Destab Calcium Carbonate 90S ultra | Alkalizer | 28.36 |
| PVPP XL | Disintegrant | 5.46 |
| Cellulose MK GR | Filler | 12.18 |
| Aerosil 200 PH | Glidant | 0.43 |
| Magnesium Stearate | Lubricant | 0.84 |
| Tablet core weight | | 230 mg |

HPMC Coating (Basic lacquer composition form Colorcon Ldt, UK, known as Opadry):

TABLE 8

Composition HPMC Coating 75 mg of the compound of formula (I)-film coated tablet

| Ingredient | % w/w |
| --- | --- |
| Basic coat White | 2.25 |
| Basic coat Yellow | 0.89 |
| Basic coat Red | 0.20 |
| Basic coat Black | 0.02 |
| Film coat weight | 8 mg |

Preparation

The composition is prepared by weighing and mixing the compound of formula (I) (Form poly-D) and excipients except half of the magnesium stearate and Aerosil. The mixture is sieved and mixed and sieved magnesium stearate is added. The composition is blended and dry granulated by roller compaction. The granules are blended with the Aerosil and subsequently the remaining magnesium stearate. This mixture is blended and compressed into tablets. The tablets are dedusted and subsequently coated with HPMC containing lacquer in a coating pan. The tablet batch size is about 9.2 kg. The in-process controls are as follows (target values):

TABLE 9

| In-process control resultsControl | Range | unit |
| --- | --- | --- |
| Tablet press compression force | 10.5 | kN |
| Tablet size | 8 round | mm |
| Tablet thickness | 3.5-3.9 | mm |
| Crushing strength | >60 | N |
| Friability (500 rpm) | <0.8 | % |
| Disintegration time | <10 | Min |

Example 9

Testing of Example 7 and Example 8

TABLE 10

In-process control results Example 7 and Example 8

| Control Dosage form | Example 7 Film-coated tablet | Example 8 Film-coated tablet |
| --- | --- | --- |
| Tablet size mm | 6 | 8 |
| Tablet thickness mm | 2.5 | 3.7-3.8 |
| Crushing strength N | 35-40 | 47 |
| Friability (500 rotations) % | 0.2 | 0.1-0.5 |
| Disintegration time Min | 1.0-1.45 | 0.4-0.5 |

Dissolution Profile Dissolution method: Basket 100 rpm Na Phosphate buffer pH7.4 900 ml (Method see Error! Reference source not found.)

TABLE 11 dissolution release profile at pH 7.4 for Example 7
Dissolution pH 7.4 Film-coated tablet (FCT) 30 mg of Example 7

| Time min | mean 30 mg FCT n = 6 | Std Dev | CV % |
| --- | --- | --- | --- |
| 0 | 0 | 0 | 0 |
| 15 | 88.4 | 3.7 | 4.2 |
| 30 | 96.1 | 2.3 | 2.4 |
| 45 | 97.7 | 1.8 | 1.8 |
| 60 | 98.2 | 1.6 | 1.6 |
| 75 | 99.0 | 1.4 | 1.4 |

Figure 8:
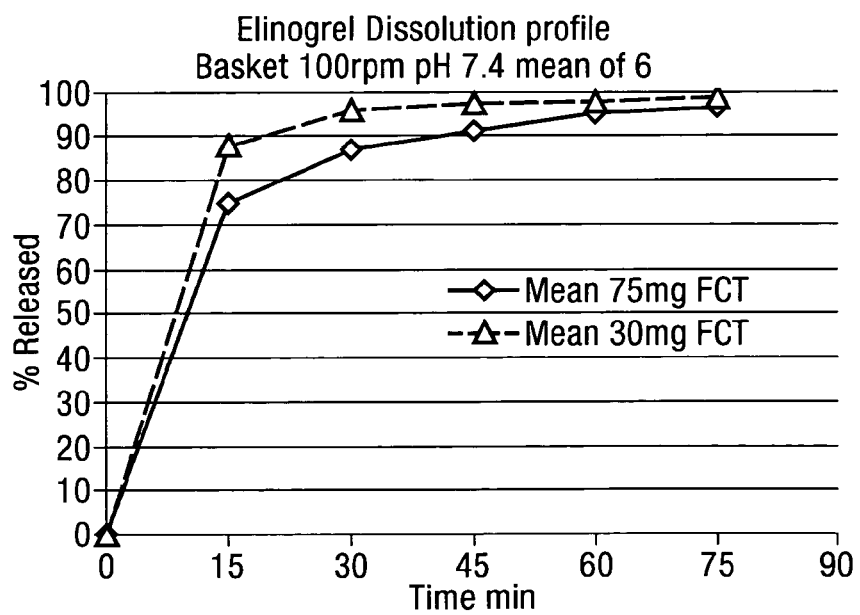
FIG. 8 shows the dissolution release profiles at pH 7.4 for Example 7 and Example 8 processed with roller compaction.

Std Dev = Standard Deviation (see FIG. 8)
CV = Coefficient variation = standard deviation/mean, equivalent to relative standard deviation

TABLE 12 dissolution release profile at pH 7.4 for Example 8
Dissolution pH 7.4 Film-coated tablet 75 mg

| Time min | mean 75 mg FCT | Std Dev | CV % |
| --- | --- | --- | --- |
| 0 | 0 | 0 | 0 |
| 15 | 75.0 | 7.7 | 10.3 |
| 30 | 87.1 | 5.5 | 6.3 |
| 45 | 91.3 | 4.1 | 4.5 |
| 60 | 95.2 | 1.0 | 1.1 |
| 75 | 96.6 | 2.3 | 2.3 |

(see FIG. 8)
Std Dev = Standard Deviation
CV = Coefficient variation = standard deviation/mean, equivalent to relative standard deviation Dissolution of both formulations is fast and with low variability and well within the USP standard limits of Q75% after 45 minutes.

---

(TABLE 6-continued, page 29)

TABLE 6-continued

In-process control results

| Control | Range | unit |
| --- | --- | --- |
| Tablet thickness | 2.4-2.8 | mm |
| Crushing strength | >30 | N |
| Friability (500 rpm) | <0.8 | % |
| Disintegration time | <10 | Min |

Dissolution Profile multi-pH (Method see Error! Reference source not found.)

TABLE 13

Results multi-pH dissolution Film-coated tablet 30 mg (Example 7 n = 3)

| Time min | mean % released | Std-Dev | CV % |
|---|---|---|---|
| 0 | 0 | 0.0 | 0.0 |
| 30 | 2.0 | 0.5 | 27.2 |
| 45 | 46.7 | 1.1 | 2.5 |
| 75 | 83.6 | 2.8 | 3.3 |
| 105 | 96.2 | 4.4 | 4.6 |
| 120 | 97.3 | 4.5 | 4.7 |
| 150 | 101.6 | 5.4 | 5.3 |

Std Dev = Standard Deviation
CV = Coefficient variation = standard deviation/mean, equivalent to relative standard deviation

TABLE 14

Results multi-pH dissolution Film-coated tablet 75 mg (Example 8 n = 3)

| Time | mean % released | Std Dev | CV % |
|---|---|---|---|
| 0 | 0.0 | 0.0 | 0.0 |
| 30 | 1.2 | 0.2 | 18.7 |
| 45 | 51.6 | 1.5 | 2.9 |
| 75 | 85.0 | 1.1 | 1.3 |
| 105 | 94.9 | 1.3 | 1.4 |
| 120 | 95.7 | 1.0 | 1.1 |

Figure 7:
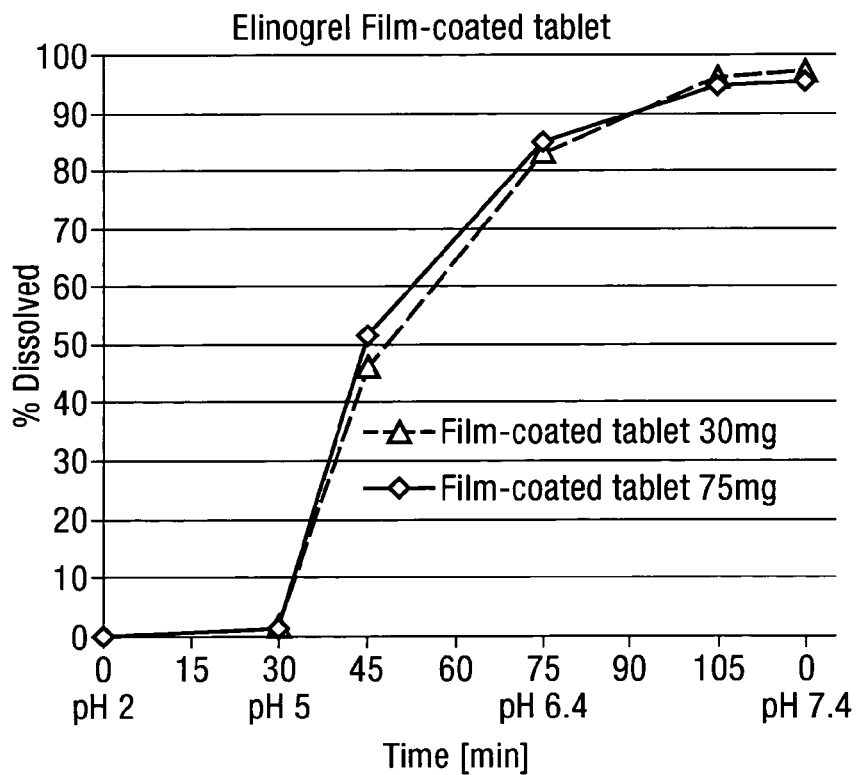
FIG. 7 shows the multi-step pH dissolution release profiles for Example 7 and Example 8 processed with roller compaction.

(see FIG. 7)
Std Dev = Standard Deviation
CV = Coefficient variation = standard deviation/mean, equivalent to relative standard deviation The dissolution profile of both dosage strengths are very similar.

Example 10

HPLC Method

Identity, assay and degradation products by HPLC
Principle RP HPLC with UV detection
Reagents
Acetonitrile Gradient grade, e.g. Merck 1.0030
Water Demineralized, e.g. from Nanopure or equivalent di-Ammonium hydrogenphosphate≥99.0% e.g. Merck 1.01207.0500
Ammonium hydroxide Concentrated 28%., for analysis e.g. Sigma 338818-5 ml (Ampoule)
Solvent Acetonitrile/Water (50/50 v/v)
di-Ammonium hydrogenphosphate buffer pH 9.0 25 mmol/L
Dissolve 3.3 g (25 mmol) of di-Ammonium hydrogenphosphate in 1000 ml of water, adjust the pH value to 9.0 using ammonium hydroxide conc. (Ampoule)
Equipment
Apparatus HPLC with UV detection e.g. HP 1200 (Agilent)
Column XSELECT CSH C18 3.5 μm
Length 150 mm, internal diameter 3.0 mm or equivalent column and particle size
Chromatographic Conditions
Mobile phase A: di-Ammonium hydrogenphosphate buffer 25 mmol/L pH 9.0 B: Acetonitrile

TABLE 15

| HPLC gradient | | |
|---|---|---|
| Time [min.] | Phase A [%] | Phase B [%] |
| 0.0 | 90 | 10 |
| 2.0 | 90 | 10 |
| 18.0 | 80 | 20 |
| 38.0 | 73 | 27 |
| 39.0 | 73 | 27 |
| 39.1 | 90 | 10 |
| 42.0 | 90 | 10 |

Flow rate 1.0 ml/min
Detection UV 250 nm
Column temperature 50° C.
Auto-sampler temperature 20° C.
Needle wash/wash vial Solvent
Injection volume 5 μl of the test and reference solutions, equivalent to about 1 μg of the compound of formula (I) in the reference solution
Procedure
No. of dosage units Individually test a minimum of 10 units
Test stock solution (TSS) Transfer 10 dosage units into a volumetric flask according to Table 16, fill the flask to about 50% of its nominal content with solvent and sonicate for about 30 min.
Shake the solution for 15 minutes.
After shaking, fill the flask with solvent to the mark, mix well and centrifuge an aliquot for about 15 minutes at 4000 rpm until the supernatant is clear.

TABLE 16

HPLC Test Solutions (TTS)

Preparation of test solutions (TSS) for assay and degradation products

| | | Dosage strength | | | | | | | |
|---|---|---|---|---|---|---|---|---|---|
| | | 0 mg | 25 mg | 30 mg | 40 mg | 50 mg | 60 mg | 75 mg | 150 mg |
| TSS | Volumetric flask (ml) | 500 | 250 | 250 | 250 | 500 | 500 | 500 | 500 |
| TS | Volume of TSS (ml) | 15 | 8 | 7 | 5 | 15 | 7 | 10 | 5 |
| | Volume of volumetric flask (ml) | 100 | 50 | 50 | 50 | 100 | 50 | 100 | 100 |
| | Dilution ratio | 6.667 | 6.250 | 7.143 | 10 | 6.667 | 7.143 | 10 | 20 |

TABLE 17

HPCL Test Solutions (TS)

Preparation of the test solutions (TS) for assay and degradation products (Hamilton)

| | | Dosage strength | | | | | | | |
|---|---|---|---|---|---|---|---|---|---|
| | | 0 mg | 25 mg | 30 mg | 40 mg | 50 mg | 60 mg | 75 mg | 150 mg |
| TSS | Volume of stock solution (µl) 250 µl sample syringe | 150 | 160 | 140 | 100 | 150 | 140 | 100 | 50 |
| TS | Volume of solvent (µl) 2.5 ml reagent syringe | 850 | 840 | 860 | 900 | 850 | 860 | 900 | 950 |
| Dilution ratio | | 6.667 | 6.250 | 7.143 | 10 | 6.667 | 7.143 | 10 | 20 |

Test solution (manually) Pipette the volume of TSS specified in Table 16 into the volumetric flask specified. Fill up to the mark with solvent and mix.

Concentration of the free acid of formula (II): 0.15-0.17 mg/ml

Water (Karl-Fischer)

Principle

Titrimetric Karl Fischer method.

Reagents

Titrimetric standard Di-sodium tartrate dihydrate, ACS grade, e.g. Merck, cat. no. 106664, containing 15.66% of water.

Titrant Hydranal—Titrant 2, Riedel de Haen, cat. no. 34811, or equivalent pyridine free reagent.

Solvent Hydranal—Solvent, Riedel de Haen, cat. no. 34800, or equivalent pyridine free solvent.

Equipment

Apparatus E.g. Metrohm 784 KFP Titrino, Methrom A G, Herisau, C H.

Burette Nominal volume of 5 ml.

Standardization

Perform the factor determination at least three times.

Weigh 30-60 mg of titrimetric standard accurately at least to 0.1 mg, dissolve it immediately in 40 ml of pre-titrated solvent and titrate to the endpoint.

Calculation

Water equivalence factor, f, of the titrant.

$$F = m_s \times W_s$$

$$A_s \times 100$$

Where $m_s$ = Mass of titrimetric standard in mg.

$W_s$ = Water of titrimetric standard in percent.

$a_s$ = Volume of titrant in ml for the standardization.

If the values found for the factor do not differ by more than 1.0° A), substitute the mean value as f in the formula for the percentage of water.

Reference Solution

Weigh the reference substance (compound of formula (I)) as accurately to 0.01 mg into a volumetric flask, dissolve in with 4% solvent Acetonitrile/Water 7/3 and dilute to volume with test medium. Weights and volumes see Table 18 below.

TABLE 18

HPLC Reference Solution

| Dosage (mg) | Weight (mg) | Volume (ml) |
|---|---|---|
| 25 | 15.0 | 500 |
| 30 | 18.0 | 500 |
| 40 | 12.0 | 250 |
| 50 | 15.0 | 250 |
| 60 | 18.0 | 250 |
| 75 | 22.5 | 250 |
| 150 | 18.0 | 100 |

If a new reference substance is used, the weighing must be adapted to the new content of the reference substance.

Evaluation

Determine the absorbance of the test solutions using a suitable spectrophotometer. If the results are calculated with the reference solution, additionally determine the absorbance of the reference solution.

TABLE 19

Cell (Quartz)

| Dosage (mg) | Cell (cm) | | |
|---|---|---|---|
| 25 | 1.0 | 0.5 | |
| 30 | 1.0 | 0.5 | |
| 40 | 0.5 | 0.25 | |
| 50 | 0.5 | 0.25 | 0.2 |
| 60 | 0.5 | 0.25 | 0.2 |
| 75 | 0.25 | 0.2 | |
| 150 | 0.2 | 0.1 | |

Reference: Test Medium

Wavelength 325 nm

Calculation, using the reference solution $D_n$ = Dissolution of Elinogrel form (I), after test interval from start to n-th sampling point in cumulated percentage of the declared content.

$$D_n = D_{un_n} + \frac{V_W}{V_T} \times \sum_{i=1}^{n-1} D_{un_i}$$

$$D_{un_i} = \frac{A_{Ti} \times m_R \times V_T \times C_R}{A_R \times V_R \times m_D \times SF}$$

Calculation, using the A1%

$$D_{un_i} = \frac{A_{Ti} \times V_T \times 10 \times 100}{A_R \times V_R \times m_D \times SF}$$

$$A1\% = \frac{A_R \times V_R \times 10 \times 100}{m_R \times C_R \times d}$$

Standard value for Elinogrel form (I)=472.6 (465.5-479.7) The standard value corresponds to a value of 507.1 (499.5-514.7) if the salt factor is taken into account for the calculation of the A1% SF. In this case the following formula applies:

$$D_{un_i} = \frac{A_{Ti} \times V_T \times 10 \times 100}{A1\%_{SF} \times m_D \times d}$$

Where
n Number of sampling points
$D_{un}$ Dissolution of Elinogrel, in percentage of the declared content uncorrected regarding the volume withdrawn.
$D_{un\ n}$ Uncorrected dissolution of the compound of formula (I)), at the last considered sampling point
$D_{un\ i}$ Each of the individual Dun at the respective sampling time points, indexed by i
i Running factor for indexing the sampling time points. It starts with 1 for the first sampling time point and ends with n for the last considered sampling point.
A1% Specific absorbance of a 1% (m/v) solution at 325 nm normalized to a cell path of 1.0 cm
$A_{Ti}$ Absorbance of the compound of formula (I) at the absorbance maxima at about 325 nm in the test solution at sampling time point i.
$m_R$ Mass of reference substance in mg
$V_T$ Volume of the test solution in ml
$C_R$ Declared content of the reference substance in percent
$A_R$ Absorbance of the compound of formula (I) at the absorbance maxima at about 325 nm in the reference solution.
$V_R$ Volume of the reference solution in ml
$m_D$ Declared drug substance content in mg per dosage form
SF Salt/acid factor Mod D (1.073)
$V_w$ Volume withdrawn in ml
d Cell thickness in cm
10 Conversion factor mg/ml to percent
100 Conversion factor to percent
Assessment In accordance with the acceptance table in USP <711>, "Dissolution." Testing should be continued to stage $S_2$ unless the results conform at stage $S_1$.

Example 11

Dissolution Test

Dissolution Test Method pH 7.4
Principle
Measurement of the amount of drug substance dissolved in a dissolution apparatus 1 (basket) according to Ph. Eur. 2.9.3 "Dissolution for Solid Dosage Forms" or USP <711>"Dissolution". Determination by HPLC detection.

Reagents
NaH2PO4*H2O Sodium dihydrogen phosphate monohydrate (e.g. Merck p.a. 1.06346 or equivalent)
Deionized water
NaOH 10N e.g. Fluka 38214 or equivalent
NaOH 2N e.g. Fluka 71474 or equivalent
HCl 2N e.g. Fluka 35327 or equivalent
Phosphate buffer pH 7.4
Dissolve 6.9 g of NaH2PO4*H2O and 3.5 ml of NaOH 10N in 1000 ml water. If necessary adjust the pH value to 7.4±0.05 with NaOH 2N or HCl 2N. The medium is degassed before use.
Dissolution Conditions
Basket method according to USP <711>, "Dissolution"
Speed of rotation 100±4 rpm
Test medium Phosphate buffer pH 7.4
Volume of test medium 900 ml
Temperature 37±0.5° C.
Number of units tested Examine the prescribed number of units according to the acceptance table of the current USP (minimum of 6, 1 per vessel).
Procedure
Test solution After 45 minutes withdraw 10 ml of the solution and filtrate through a glass fiber filter (e.g. Whatman GF/F 0.7 μm or equivalent). Optionally a dissolution profile can be measured. In this case it is recommended to sample after at least 15, 30, 45, 60 and 75 minutes (infinity test). The sample withdrawal has to be replaced by test medium. Determination of the dissolved drug substance according to the HPLC method described In Example 10
Dissolution Test Method Multi pH

TABLE 20

| Multi pH Dissolution Method Multi pH Dissolution Method USP 2 (Paddle) 50 rpm, 37° C. | | | | |
|---|---|---|---|---|
| Stage | Target pH | Buffer to add (pH, molarity) | Duration (min) | Sampling time (min) |
| 1 | 2 | pH 2.0 0.01M HCl | 30 | 15, 30 |
| 2 | 5 | pH 5.2, Sodium Acetate | 45 | 15, 30, 45 |
| 3 | 6.4 | pH 6.8, Sodium Phosphate | 45 | 15, 30, 45 |
| 4 | 7.4 | pH 8.0, Sodium Phosphate | 45 | 15, 30, 45 |
| 5 | 8.2 | 10N Sodium Hydroxide | 18 hr | 15, 18 hr |

Stage 5: 250 rpm (infinity test).
Sampling volume: 5 ml without medium replacement.

The methods describes the maximum sampling times. The minimum sampling times are at least 1 sampling point in stage 1 to 4.

Example 11

Saturation Solubility

Method:
The sample solubility was determined using shake-flask methodology with sample quantification by UV spectroscopy in a series of different media; sodium acetate buffer (pH 4.52); sodium phosphate buffer (pH 6.81); fasted state simulated intestinal fluid (FaSSIF, pH 6.5); fed state simulated intestinal fluid (FeSSIF, pH 5.0) and simulated gastric fluid (SGF, pH 2.1). The FaSSIF and FeSSIF solutions were prepared using Phares SIF powder according to the formulation instructions and the SGF solution was prepared using the guidelines provided. The molar extinction coefficients of the polymorph A were measured at a sample concentration of 25.0 µM in each of the solubility media. Due to the insolubility of the sample at low pH, accurate MECs could not be obtained in the SGF solution. The MECs determined in the acetate buffer (pH 4.5) were therefore used to ascertain the solubility of the sample in the SGF solution. To determine the solubility, 2.0 ml of solubility medium was added to an appropriate weight of pure polymorph A (5.0-10.9 mg), producing a suspension that was subsequently agitated for 72 hours on an electronic shake-plate. After agitation, the suspensions was left for a period of 96 hours to sediment/equilibrate, before an appropriate amount of supernatant was extracted by pipette, filtered under vacuum through a 0.2 µm PVDF filter plate, and its absorption spectrum recorded. The pH and temperature of the supernatant were measured on a SiriusT3 instrument. The solubility was subsequently determined from the measured absorption of the supernatant solution and the previously determined molar extinction coefficients using a wavelength range of 280-320 nm (310-330 nm for the solubility in FaSSIF and FeSSIF). The sample was analysed in duplicate in each of the solubility media, the results of which are recorded in the Table 21. It should be noted that the resulting pH in some of the experiments has shifted from the pH of the solubility media due to the dissolution of the sample. The reported solubility values therefore correspond to the final pH measured, and is reported in the Table 21. Due to the recommended use within 48 hours of preparation, the solubility in FaSSIF and FeSSIF was determined after both 48 hours and 7 days. 5.0 ml of FaSSIF/FeSSIF were added to 30 mg of the sample and agitated for 24 hours. After this time 2 ml of the suspension was extracted and left to sediment/equilibrate for a further 24 hours before filtration and analysis. The remaining solution continued to be agitated for a total of 72 hours, and then left to sediment/equilibrate for a further 96 hours before analysis (identical to the other experiments). The MECs obtained in FaSSIF and FeSSIF after 48 hours have been used to process the data for both the 48 hour and 7 day experiments. The FaSSIF solution became opaque after 48 hours, so any necessary dilutions needed for the 7 day experiment solubility determination were carried out using deionised water.
Result:

The saturation solubility in buffered solutions and simulated fluids at around pH 7 is highest for polymorph poly-D>B>A>free acid.

The compound of formula (I) in crystalline form poly-D shows a surprisingly higher dissolution rate in buffered aqueous media and simulated gastric or intestinal fluids compared with other crystalline forms of the compound of formula (I) and compared with the free acid which has the structural formula (II)

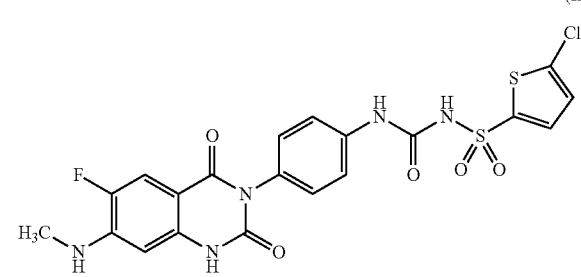

(II)

Example 12

Wettability

Method:
Contact angel instrument: EasyDrop DSA15E (Krüss, Hamburg, Germany)
Syringe: NE44, diameter of needle 0.5 mm (Krüss, Hamburg, Germany)
Standards (Krüss, Hamburg, Germany): CP24 20007107, contact angle Gauge#4=30.00°+/−0.3, Gauge#5=60.00°+/−0.3, Gauge#6=120.00°+/−0.3

The powder was pressed (approx 50 mg powder, 3 tons, 2 min) in tablets and analyzed by contact angle measurement. The angel between the solid and the liquid is measured after 0 and up to 60 seconds using water.

All determinations used the above method and the limit for the standards measurements are well within the given limits.

The critical angle is estimated around 50° (>50° hydrophob <50° hydrophil) according to BC Lippold, A. Ohm, Correlation between wettability and dissolution rate of pharmaceutical powders, International Journal of Pharmaceutics, 28 (1986) 67-74.

TABLE 21

Saturation Solubility Results

| Drug substance/<br>Buffer MEAN N = 2 | pH | The compound of formula (I), form A (µg/ml) | pH | The compound of formula (I), form B (µg/ml) | pH | The compound of formula (I), form poly-D (µg/ml) | pH | The free acid of formula (II) (µg/ml) |
|---|---|---|---|---|---|---|---|---|
| Na-Acetate pH 4.5 | 4.81 | 0.48 | 4.81 | 0.40 | 4.82 | 0.86 | 4.53 | 0.89 |
| Na Phosphate pH 6.8 | 6.94 | 20.25 | 7.02 | 25.95 | 7.08 | 94.55 | 6.80 | 11.30 |
| FaSSIF pH 6.5-1w | 6.93 | 107.00 | 6.97 | 132.50 | 7.00 | 166.50 | 6.42 | 25.20 |
| FeSSIF pH 5.0-1w | 5.15 | 2.76 | 5.16 | 2.49 | 5.17 | 6.94 | 4.97 | 6.00 |
| SGF pH 2.1 | 4.74 | 2.24 | 5.05 | 19.14 | 6.34 | 46.10 | 2.21 | 0.48 |

TABLE 22

Contact Angle Measurement Results

| Polymorph | Batch | n= | 0 sec | 10 sec | 20 sec | 30 sec | 60 sec |
|---|---|---|---|---|---|---|---|
| Free acid | C0015 | 2 | 65.9 | | | 60.8 | 60.1 |
| B | 28004677 | 2 | 72.4 | | | 54.6 | 53.5 |
| A | 913008 | 2 | 78.8 | | | 53.3 | 51.0 |
| Poly-D | C0010 | 1 | 53.3 | 28.2 | 22.9 | 20.6 | 15.2 |
| B | 1019024 | 2 | 79.7 | | | 55.2 | 52.8 |
| Poly-D | 1013003 | 2 | 55.7 | 27.7 | 16.1 | | |
| Poly-D | 1013022 | 1 | 78.1 | 33.4 | 21.7 | | |

Results:

The contact angle measurements show the significant difference in the surface hydrophobicity between polymorph B and A that are hydrophob compared to polymorph poly-D which is hydrophilic.

Example 13

Super-Saturation Measurements and Stabilization

Super-Saturation Experiments

Super-saturation measurements are well known as can be seen from the published literature [1—Stuart, M. Box, K. Chasing equilibrium: measuring the intrinsic solubility of weak acids and bases. Anal. Chem. 2005, 77(4), 983-990; 2—Box, K J. Völgyi, G. Baka, E. Stuart, M. Takács-Novák, K. Corner, J E A. Equilibrium vs. kinetic measurements of aqueous solubility, and the ability of compounds to supersaturate in solution—a validation study. J. Pharm. Sci. 2006, 95, 1298-1307; 3—Sköld, C. Winiwarter, S. Johan Wernevik, J. Bergström, F. Engström, L. Allen, R. Box, K. Corner, J. Mole, J. Hallberg, A. Lennernäs, H. Lundstedt, T. Ungell, A-L. Karlén, A. Presentation of a Structurally Diverse and Commercially Available Drug Data Set for Correlation and Benchmarking Studies. J. Med. Chem. 2006, 49(23), 6660-6671; 4—Llinás, A. Burley, J C. Box, K J. Glen, R C. Goodman, J M. J. Diclofenac Solubility: Independent Determination of the Intrinsic Solubility of Three Crystal Forms. Med. Chem.; 2007, 50 (5), 979-983; 5—Llinás, A. Box, K J. Burley, J C. Glen, R C. Goodman, J M. J. A new method for the reproducible generation of polymorphs: two forms of Sulindac with very different solubilities. J. Applied Crystallography, 2007, 40(2), 379-381. 6—Box K et al, Using Measured pKa, Log P and Solubility to Investigate Supersaturation and Predict BCS Class, Current Drug Metabolism, 2008, 9, 869-878]

Using the cited CheqSol measurement, e.g. the polymorph B of the compound of formula (I) exhibits a super-saturation ratio of 363, and the free acid of formula (II) a super-saturation ratio of 178.

The definitions of the solubility are as follows:

1—kinetic solubility is the concentration of a compound in solution at the time when an induced precipitate first appears
2—equilibrium solubility (also called thermodynamic solubility) is the concentration of compound in a saturated solution when excess solid is present, and solution and solid are at equilibrium
3—intrinsic solubility [Hörter, D.; Dressman, J. B. Adv. Drug Deliv. Rev., 1997, 25, 3-14] is the equilibrium solubility of the free acid or base form of an ionisable compound at a pH where it is fully un-ionized The super-saturation ratio is calculated as the ratio of kinetic solubility divided by the Intrinsic Solubility. Examples of drugs with different super-saturation ratios are listed in Table 23.

TABLE 23

Supersaturation ratio of various drugs [excerpt form Box K et al, Using Measured pKa, LogP and Solubility to Investigate Supersaturation and Predict BCS Class, Current Drug Metabolism, 2008, 9, 869-878]

| Compound | pKa(s) A = acid B = Base | LogP | LogS0 | Super-saturation ratio | BCS Class |
|---|---|---|---|---|---|
| 1-naphthol | A 9.175 | 2.85 | −1.98 | 1.37 | Ia |
| 2-naphthoic acid | A 3.884 | 3.28 | −3.78 | 2.05 | IIa |
| 4-hydroxybenzoic acid | A 4.32 A 8.94 | 1.58 | −1.45 | 1.55 | Ia |
| Alprenolol | B 9.477 | 3.1 | −2.63 | 2.2 | I |
| Amantadine | B 10.48 | 2.41 | −1.86 | 1.23 | I |
| Amiodarone | B 8.73 | 7.57 | −8.17 | 0.7 | IV |
| Amitriptyline | B 9.3 | 5.04 | −4.39 | 1.02 | II |
| Amodiaquin | B 7.37 B 8.24 A 11.49 | 4.2 | −5.94 | 21.9 | IIa |
| Astemizole | B 5.73 B 8.48 | 5.7 | −5.93 | 1.72 | IIa |
| Atenolol | B 9.54 | 0.22 | −1.29 | | III |
| Benzocaine | B 2.39 | 1.89 | −2.23 | 1.14 | 0 |
| Benzoic Acid | A 3.99 | 1.87 | −1.61 | 1.25 | Ia |
| Carprofen | A 4.247 | 4.29 | −4.71 | 2.41 | II |
| Chlorpheniramine | B 3.87 B 9.28 | 3.39 | −2.66 | 1.08 | I |
| Chlorpromazine | B 9.24 | 5.4 | −5.08 | 1.0 | II |
| Chlorprothixene | B 9.52 | 5.48 | −6.3 | 8.41 | IIa |
| Chlorzoxazone | A 8.18 | 2.11 | −2.61 | 2.91 | II |
| Deprenyl | B 7.48 | 2.9 | −2.52 | 1.04 | I |
| Desipramine | B 10.08 | 4.21 | −3.44 | 0.95 | I |
| Diclofenac | A 4.032 | 4.51 | −5.45 | 41.9 | II |
| Diltiazem | B 8.02 | 2.89 | −2.94 | 1.05 | I |
| Diphenhydramine | B 9.08 | 3.44 | −2.93 | 1.09 | I |
| Flufenamic Acid | A 3.968 | 5.56 | −5.35 | 9.71 | IIa |
| Fluoxetine | B 10.09 | 4.61 | −3.92 | 0.92 | Ia |
| Flupenthixol | B 3.29 B 7.57 | 4.68 | −4.02 | 0.85 | I |
| Flurbiprofen | A 4.01 | 4.16 | −4.11 | 4.3 | II |
| Furosemide | A 3.60 A 10.15 | 2.56 | −4.23 | 4.97 | IV |
| Haloperidol | B 8.42 | 4.3 | −5.47 | 53.8 | II |
| Ibuprofen | A 4.35 | 3.97 | −3.61 | 1.58 | II |
| Imipramine | B 9.54 | 4.42 | −4.21 | 1.01 | I |
| Lidocaine | B 7.95 | 2.44 | −1.85 | 1.35 | I |
| Maprotiline | B 10.33 | 4.85 | −4.69 | 4.75 | I |
| Meclizine | B 2.23 B 7.24 | 6.2 | −6.49 | 0.74 | IV |
| Meclofenamic Acid | A 4.10 | 5.9 | −6.86 | 6.88 | II |
| Mefenamic Acid | A 4.221 | 5.33 | −6.34 | 46.8 | II |
| Metoclopramide | B 9.24 | 2.74 | −3.59 | 4.98 | I |
| Metoprolol | B 9.56 | 1.95 | −1.21 | | I |
| Miconazole | B 6.316 | 5.34 | −5.62 | | IV |
| Nadolol | B 9.696 | 0.71 | −1.57 | 4.00 | III |
| Naproxen | A 4.18 | 3.24 | −4.14 | 3.12 | II |
| Niflumic Acid | B 2.26 A 4.44 | 3.88 | −4.47 | 6.03 | IIa |
| Nortriptyline | B 10.21 | 4.39 | −3.99 | 1.02 | I |
| Orphenadrine | B 9.037 | 3.84 | −3.17 | 0.91 | Ia |
| Papaverine | B 6.39 | 2.95 | −4.3 | 18.3 | II |
| Paracetamol | A 9.52 | 0.46 | −1 | 1.72 | III |
| Bendroflumethiazide | A 8.46 A 9.73 | 1.95 | −4.33 | 7.53 | II |
| Benzthiazide | A 6.674 A 9.208 | 1.73 | −4.83 | 6.71 | IVa |
| Ciprofloxacin | A 6.234 B 8.579 | −1.08 | −3.6 | 8.96 | IV |
| Famotidine | B 6.77 A 11.01 | −0.81 | −2.66 | 7.96 | III |
| Flumequine | A 6.37 | 1.72 | −3.88 | 3.5 | IIa |
| Folic Acid | B 2.33 A 3.87 A 4.76 A 7.98 | 0.2 | −5.31 | 10.2 | IV |
| Glipizide | A 5.13 | 2.58 | −5.49 | 48.6 | II |
| Hydrochlorothiazide | A 8.75 A 9.88 | −0.07 | −2.68 | 3.85 | III |
| Loperamide | B 8.898 | 4.87 | −7.13 | 121.0 | IV |
| Nitrofurantoin | A 7.05 | −0.54 | −3.33 | 3.98 | II |
| Norfloxacin | A 6.324 B 8.575 | −1.03 | −2.75 | 5.91 | IV |
| Piroxicam | B 1.87 A 5.29 | 1.98 | −4.75 | 43.0 | II |
| Sulfamerazine | B 2.22 A 6.81 | 0.15 | −3.1 | 3.44 | IIa |
| Sulfasalazine | A 2.351 A 7.998 A 10.885 | 3.61 | −6.28 | | IV |
| Sulfathiazole | B 2.124 A 7.168 | 0.07 | −2.7 | 1.84 | IIIa |

TABLE 23-continued

Supersaturation ratio of various drugs [excerpt form Box K et al, Using Measured pKa, LogP and Solubility to Investigate Supersaturation and Predict BCS Class, Current Drug Metabolism, 2008, 9, 869-878]

| Compound | pKa(s) A = acid B = Base | LogP | LogS0 | Super-saturation ratio | BCS Class |
|---|---|---|---|---|---|
| Terfenadine | B 9.25 | 5.42 | −7.74 | 8.34 | IV |
| Tetracycline | A 3.34 A 7.44 B 9.05 | −1.4 | −3.09 | 23.3 | III |
| Trichlormethiazide | A 6.693 A 9.707 | 0.97 | −3.41 | 15.0 | IIIa |

TABLE 24

Supersaturation Results for the compound of formula (II), Salts and Polymorphs thereof and formula (I)

| Polymorph | intrinsic solubility nMol/L | ng/ml | kinetic solubility nMol/L | ng/ml | ratio super saturation |
|---|---|---|---|---|---|
| K-salt-Form A | 30.5 | 15.9 | 12570 | 6571 | 412 |
| K-salt-Form B | 21.6 | 11.3 | 7845 | 4110 | 363 |
| Free acid | 44.6 | 23.4 | 7964 | 4173 | 179 |
| Na salt | 40.8 | 21.4 | 11670 | 6101 | 286 |

The supersaturation ratio measured for the compound of formula (II) free acid or potassium and sodium salts is higher than all published ratios (Table 23) as shown in Table 24.

Supersaturation Stabilization Experiments

Typically the higher the super saturation, the faster and the more extensive is the precipitation which occurs. On the other hand, higher bioavailability may be achieved by using excipients which interact with the drug in the super-saturated state. In this super-saturated state, precipitation is inhibited and/or delayed, thus leading to higher luminal drug concentrations in vivo of the dissolved drug.

Surprisingly, subsequent investigations using the described CheqSol measurement lead to the findings that the super-saturation of the compound of formula (II) can be preserved over a long period of time when using special pharmaceutical excipients. The present invention thus provides a pharmaceutical composition which achieves higher bioavailability of the drug substance.

Examples of such excipients are PVP K90 to drug ratio is 1:1 by weight. At pH>6.0 a stable super-saturation of about 17-86 fold for 66 hours is observed.

The solubility measured by Sirius CheqSol at pH 6.0 is 9.9 ug/ml. After 66 hours the pH shifted to 7.2. At this pH the compound of formula (II) solubility is approx. 170 ug/ml compared to 860 ug/ml after 67 h with PVP. This leads to 17 or 86 fold super-saturation ratio. The examples using a 1:1 drug to excipient ratio by weight that has been investigated are listed in Table 25.

Solubility-Excipient Screening:

The solubility behavior of the compound of formula (II) in 0.15 M aqueous KCl was screened in the presence of a variety of excipients using the Sirius CheqSol method. In all experiments, the compound of formula (II) and excipient were present at a 1:1 weight ratio. For each excipient, Form A of the potassium salt was titrated at an initial concentration of ~1 mg/ml from pH 12 to low pH with 0.5 M HCl. A UV-turbidity probe was used to detect the presence of sample precipitate and all experiments were carried out according to standard CheqSol procedure.

TABLE 25

Kinetic and Instrinsic Solubility of a polymorph of the compound of formula (I) with polymers

| Chemical Class | Tradename examples | Quality | Kinetic solubility uMol/L | pH first precipitation occurs |
|---|---|---|---|---|
| Form A of the potassium salt (Reference) | | | 12.57 | 5.3 |
| HPMC—Hydroxy propylmethyl-cellulose | Pharmacoat | 603 | 18.48 | 4.9 |
| PVP—Polyvinyl-pyrrolidone | PVP | K90 | 181.5 | Not observed |
| Poly acrylate | Eudragit | L100-55 | | 5.2 |
| HPC—Hydroxy propyl-cellulose | Klucel | EF | 17.31 | 4.9 |
| Poloxamer 188 | Pluronic | F68 | 2.74 | 5.8 |

The kinetic solubility increases extremely when using PVP and to a much lesser extent when using other pharmaceutical polymers like HPMC and HPC. The surfactant Poloxamer 188 had a lower kinetic solubility compared to the pure drug. There is a significant range between the highest and lowest kinetic solubilities.

Example 14

Surface Tension

Method—Surface Tension determination by Kibron Delta-8 Tensiometer (microtensiometry)

Surface tension is measured with the Kibron Delta-8 tensiometer which is an 8-channel microbalance meaning that 8 samples can be measured simultaneously. Samples are prepared in standard footprint 96-well plates using 50 μL sample volumes. The technique measures the weight of the meniscus using a high performance micro balance. A thin rod is immersed into the sample and then pulled out and the maximum force is measured (also known as the Du-Nouy-Padday method, *J. Chem. Soc., Faraday Trans.* 1, 1975, 71, 1919-1931, DOI:10.1039/F19757101919). The weight of the meniscus depends only on surface tension, rod diameter, and the density of the liquid. Calibration is performed using a liquid with a known surface tension, e.g., deionised water. Surfactants/amphiphilic molecules contain both hydrophilic and hydrophobic parts. The hydrophilic part of the molecule prefers to interact with water while the hydrophobic part is repelled from water. Surface active molecules absorb at the air/water interface, decreasing surface tension. As the interface becomes saturated, the molecules start to form aggregates or micelles in the bulk of the liquid with the surface tension remaining constant. The Kibron Delta-8 records the surface tension for a serial dilution of a sample from the lowest to highest concentration, giving the concentration of the surfactant required for CMC, critical micelle concentration. The critical micelle concentration (CMC) results in a sharp transition above which the concentration of the free surfactant/amphiphile molecules remains constant. No further reduction in surface tension with increasing concentration occurs resulting in a plateau in the surface tension vs. concentration curve.

Results

Stock solutions of sample of the potassium salt of formula (I) were prepared in de-ionised water at concentrations of 1.62 mg/mL and 1.81 mg/mL. These stock solutions were used to prepare dilution series for the measurement plate. The study plate has 12 wells in one row and 8 rows having 96 wells in total.

Row A contained a known surfactant prepared in de-ionised water and double diluted in the following concentrations: A1 25 mM, A2 12.5 mM, A3 6.25 mM . . . A11 0.024 mM. Position A12 contained deionised water.

Row B contained an in-house QC sample prepared in pH2 phosphate buffer and double diluted in the following concentrations: B1 100 mM, B2 50 mM, B3 25 mM . . . B11 0.098 mM. Position B12 contained pH2 phosphate buffer.

Row C contained solutions of the potassium salt of formula (I) prepared from the 1.62 mg/mL stock. Position C1 contained 1.62 mg/mL The compound of formula (II) K+ in de-ionised water. Position C2 was a double dilution into pH6 phosphate buffer, i.e., 0.81 mg/mL. The remaining wells were further double dilutions into pH6 phosphate buffer: C3 0.40 mg/mL, C4 0.20 mg/mL . . . C11 0.0016 mg/mL. Position C12 contained pH6 phosphate buffer.

Row D was a repeat of Row C and contained solutions of the potassium salt of formula (I) prepared from the 1.62 mg/mL stock. Position D1 contained 1.62 mg/mL the potassium salt of formula (I) in de-ionised water. Position D2 was a double dilution into pH6 phosphate buffer, i.e., 0.81 mg/mL. The remaining wells were further double dilutions into pH6 phosphate buffer: D3 0.40 mg/mL, D4 0.20 mg/mL . . . D11 0.0016 mg/mL. Position D12 contained pH6 phosphate buffer.

Row E contained solutions of the potassium salt of formula (I) prepared from the 1.81 mg/mL stock. Position E1 contained 1.81 mg/mL the potassium salt of formula (I) in de-ionised water. Position E2 was a double dilution into pH9.5 borate buffer, i.e., 0.91 mg/mL. The remaining wells were further double dilutions into pH9 borate buffer: E3 0.45 mg/mL, E4 0.23 mg/mL . . . E11 0.0018 mg/mL. Position E12 contained pH9.5 borate buffer.

Row F was a repeat of Row E and contained solutions of the potassium salt of formula (I) prepared from the 1.81 mg/mL stock. Position F1 contained 1.81 mg/mL the potassium salt of formula (I) in de-ionised water. Position F2 was a double dilution into pH9.5 borate buffer, i.e., 0.91 mg/mL. The remaining wells were further double dilutions into pH9 borate buffer: F3 0.45 mg/mL, F4 0.23 mg/mL . . . F11 0.0018 mg/mL. Position F12 contained pH9.5 borate buffer.

Row G was a repeat of Row A and contained a known surfactant prepared in de-ionised water and double diluted in the following concentrations: G1 25 mM, G2 12.5 mM, G3 6.25 mM . . . G11 0.024 mM. Position G12 contained de-ionised water.

Row H contained de-ionised water.
Results:

TABLE 26

Results of pH dependent surface tension measurements

| Surface Active | T/° C. | Medium | Method | pH | CMC (mg/ml) Limit <1 mg/ml | Surface tension at CMC mN/m |
|---|---|---|---|---|---|---|
| Yes | 24.4-24.6 | pH 6.0 phosphate buffer | Micro-tensiometer | 6 | 0.1 | 62 |
| Yes | 24.1 | pH 6.5 phosphate buffer | Micro-tensiometer | 6.5 | >1.7 | 68 |
| Yes | 24.1 | pH 7.0 phosphate buffer | Micro-tensiometer | 7 | >2.7 | 65 |

TABLE 26-continued

Results of pH dependent surface tension measurements

| Surface Active | T/° C. | Medium | Method | pH | CMC (mg/ml) Limit <1 mg/ml | Surface tension at CMC mN/m |
|---|---|---|---|---|---|---|
| Yes | 24.1 | pH 7.5 phosphate buffer | Micro-tensiometer | 7.5 | >4.0 | 63 |
| Yes | 24.1 | pH 8.0 phosphate buffer | Micro-tensiometer | 8 | >3.5 | 63 |
| No | 24.4-24.6 | pH 9.5 borate buffer | Micro-tensiometer | 9.5 | n/a | |
| No | 24.4-24.6 | De-ionised water | Micro-tensiometer | | n/a | |

The potassium salt of formula (I) has no surface activity at pH9.5 in borate buffer. Sample the potassium salt of formula (I) has no surface activity when prepared in de-ionised water at concentrations of 1.6-1.8 mg/mL. The natural pH of these solutions is estimated as ~pH 8. Sample the potassium salt of formula (I) does exhibit surface activity at pH6 in phosphate buffer. The maximum surface pressure change is 11 mN/m and the critical micelle concentration is determined as 0.1 mg/mL.

Surface activity may support stabilization of super-saturation of this drug at a specific pH range.

Example 15

Pharmacokinetic Study 1

This was an open label, randomized, four-period, incomplete crossover, single center study in healthy adult volunteers. There were 4 treatments in the study: 3 doses of the FMI (given fasting or fed following a high-fat breakfast) and one reference IR capsule (given fed after a typical breakfast). The term "FMI" refers to the dosage form of Example 7 (30 mg FMI) or Example 8 (75 mg FMI).

Each subject was randomized to 1 of 18 treatment sequences, each with 4 treatment periods (Table 27). The first treatment period consisted of 1 of the 3 doses of FMI given fed, and treatment periods 2 to 4 consisted of 1 dose of IR capsule (fed) and 2 of the 3 doses of the FMI given fasted. No subject received all 3 doses of the FMI (the dose given in treatment period 1 (fed), was also given fasted in treatment periods 2 to 4), hence the study design is described as an incomplete crossover study. Each subject therefore had 2 fasting treatments with the FMI formulation, 1 fed treatment with the FMI formulation and a reference treatment (IR capsule). Seventy two subjects enrolled and were dosed in the study with 70 completers.

The study consisted of a 28-day screening period, four baseline periods (one before each treatment period), four treatment periods with a wash out period of a minimum of 5 days, followed by a study completion evaluation approximately 72 hours after the last drug administration. Subjects who met the eligibility criteria at screening were admitted to baseline evaluations. All baseline safety evaluation results were available prior to dosing.

For fasted administration, elinogrel was administered in the morning, following an overnight fast of at least 10 hours. Subjects continued to fast until 4 hours post-dose. For fed administration of FMI tablets, elinogrel was administered in the morning, within 30 minutes of a high fat breakfast (approximately 1000 calories). Subjects continued to fast until 4 hours post-dose. For fed administration of the reference (IR capsule), it was administered in the morning, within 30 minutes of a typical breakfast (approximately 500 calories). Subjects continued to fast until 4 hours post-dose.

Subjects were admitted to the study site approximately 12 hours prior to dosing in each period for baseline evaluations. Following a single dose of elinogrel, PK assessments were taken up to 48 hours post dose and safety assessments were made for up to 72 hours.

Subjects were domiciled for 24 hours post dosing for PK sample collection, at which time they were discharged from the study site. Subjects returned on the following 2 mornings for 48 hour PK and 72 hour safety samples. Following the 72 hour safety assessments of treatment period 4 (or in the case of subject discontinuation) subjects underwent study completion evaluations and were discharged from the study. Safety assessments included physical examinations, ECGs, vital signs, standard clinical laboratory evaluations, orthostatic hypotension challenges, adverse event and serious adverse event monitoring.

Below is a tabular description of how subjects were assigned to dosing groups (Table 27).

TABLE 27

Treatment sequences for the elinogrelA2123 study

| Treatment sequence | Treatment period 1 | Treatment period 2 | Treatment period 3 | Treatment period 4 |
|---|---|---|---|---|
| 1 | F1 | T1 | T2 | R |
| 2 | F2 | T2 | T3 | R |
| 3 | F3 | T3 | T1 | R |
| 4 | F3 | T3 | T2 | R |
| 5 | F2 | T2 | T1 | R |
| 6 | F1 | T1 | T3 | R |
| 7 | F1 | R | T1 | T2 |
| 8 | F2 | R | T2 | T3 |
| 9 | F3 | R | T3 | T1 |
| 10 | F3 | R | T3 | T2 |
| 11 | F2 | R | T2 | T1 |
| 12 | F1 | R | T1 | T3 |
| 13 | F1 | T1 | R | T2 |
| 14 | F2 | T2 | R | T3 |
| 15 | F3 | T3 | R | T1 |
| 16 | F3 | T3 | R | T2 |
| 17 | F2 | T2 | R | T1 |
| 18 | F1 | T1 | R | T3 |

This was a three-period, four-treatment crossover study design with an add-on food effect period (Period 1).

Treatment 1 (T1)=elinogrel 30 mg FMI dose fasting
Treatment 2 (T2)=elinogrel 75 mg FMI dose fasting
Treatment 3 (T3)=elinogrel 150 mg FMI dose fasting
Reference (R)=elinogrel 150 mg IR capsule dose fed (typical breakfast); Example 6 (Reference)
Fed treatment 1 (F1)=elinogrel 30 mg FMI dose fed (high fat breakfast)
Fed treatment 2 (F2)=elinogrel 75 mg FMI dose fed (high fat breakfast)
Fed treatment 3 (F3)=elinogrel 150 mg FMI dose fed (high fat breakfast)

Subjects will received the following treatments in a randomized order:

Treatment (T1, F1) with IR (IR=immediate release) tablet of Example 7 containing pH-modifying alkalizing agent, 30 mg in fasted and fed state.
Treatment (T2, F2) with IR (IR=immediate release) tablet of Example 8 containing pH-modifying alkalizing agent, 75 mg in fasted and fed state
Treatment (R) with 2×IR (IR=immediate release) capsule of Example 6 (Reference): 2×75 mg (150 mg) in fed state.
Treatment (T3, F3) with 2×IR (IR=immediate release) tablet of Example 8 containing pH-modifying alkalizing agent, 2×75 mg (150 mg) in fasted and fed state.

TABLE 28

PK Parameters

| PK Parameter | FMI 30 mg | | FMI 75 mg | | FMI 50 mg | | IR Cap |
|---|---|---|---|---|---|---|---|
| | Fed (n = 23) | Fasted (n = 45-46) | Fed (n = 24) | Fasted (n = 48) | Fed (n = 24) | Fasted (n = 47) | Fed R (n = 71) |
| Tmax[a] (hr) | 8.0 (5.0; 10) | 5.0 (2.0; 10) | 6.0 (4,0; 10) | 5.0 (2.0; 8.0) | 7.0 (5.0; 10) | 5.0 (3.0; 8.0) | 5.88 (3.8; 8.0) |
| Cmax (ng/mL) | 651 (360) 55% | 1670 (707) 42% | 1932 (1218) 63% | 2783 (1249) 44% | 2667 (1187) 44% | 4865 (2059) 42% | 3421 (1858) 54% |
| AUClast (hr*ng/mL) | 5114 (2910) 57% | 10547 (5266) 50% | 16170 (11087) 69% | 19055 (10171) 53% | 24610 (9719) 39% | 35227 (20419) 58% | 24374 (15271) 62% |
| AUCinf (hr*ng/mL) | 5392 (2947) 55% | 11168 (5143) 46% | 16675 (11331) 68% | 19489 (10284) 53% | 25038 (9927) 39% | 35840 (20867) 58% | 24881 (15602) 63% |
| T½ (hr) | 5.72 (1.79) 31% | 7.12 (1.80) 25% | 6.42 (2.02) 31% | 7.46 (1.58) 21% | 6.74 (1.39) 20% | 7.46 (1.50) 20% | 7.64 (1.31) 17% |

[a]Mean (SD) presented for PK parameters except for Tmax median (range) are shown and CV is expressed as percent (%).

The PK parameters in the table above show that a food effect was observed for all doses of the FMI tablet when elinogrel was administered with a high fat meal.

To evaluate the food effect, the geometric mean ratio for PK parameters of the fed versus fasted for each dose level and its 90% CI was estimated as shown in Table 29 below.

TABLE 29

Effect of food on elinogrel pharmacokinetics

| Parameter (Unit) | Treatment | N | Geometric-mean ratio (Fed/Fasted) | 90% CI |
|---|---|---|---|---|
| AUCinf (hr * ng/mL) | 30 mg fasted | 45 | 0.48 | (0.41, 0.56) |
| | 30 mg fed | 23 | | |
| | 75 mg fasted | 48 | 0.86 | (0.74, 0.99) |
| | 75 mg fed | 24 | | |
| | 150 mg fasted | 47 | 0.71 | (0.61, 0.82) |
| | 150 mg fed | 24 | | |
| AUClast (hr * ng/mL) | 30 mg fasted | 46 | 0.56 | (0.44, 0.70) |
| | 30 mg fed | 23 | | |
| | 75 mg fasted | 48 | 0.82 | (0.66, 1.02) |
| | 75 mg fed | 24 | | |
| | 150 mg fasted | 47 | 0.70 | (0.56, 0.88) |
| | 150 mg fed | 24 | | |
| Cmax (ng/mL) | 30 mg fasted | 46 | 0.42 | (0.34, 0.53) |
| | 30 mg fed | 23 | | |
| | 75 mg fasted | 48 | 0.64 | (0.52, 0.79) |
| | 75 mg fed | 24 | | |
| | 150 mg fasted | 47 | 0.52 | (0.42, 0.65) |
| | 150 mg fed | 24 | | |

The high fat meal decreased Cmax of elinogrel 30 mg, 75 mg and 150 mg doses by 58%, 36% and 48%, respectively. The high fat meal decreased AUC of elinogrel 30 mg, 75 mg and 150 mg doses by 44-52%, 14-18% and 29-30%, respectively.

There is a significant negative food effect observed with the drug substance polymorph D.

Example 17

Pharmacokinetic Study 2

This study employed an open-label, randomized, five-treatment, single-dose, five-period, crossover design in healthy male and female subjects. A total of 50 subjects were planned to be enrolled and randomized to receive one of five sequences of treatments and approximately 40 subjects were required to complete all treatment periods. A total of 43 subjects were enrolled with 37 subjects completing the study.

Each subject participated in a screening period (from 21 days prior to dosing up to 2 days prior to dosing), a baseline visit for each period (at least 12 hours preceding the dose administration), and single-dose treatment periods. Each treatment period was comprised of a dosing day and a PK assessment period up to 72 hours post-dose. An end-of-study evaluation was completed after Period 5, or at early termination. Between each dose administration, there was a washout period of at least 5 days. This washout period was based on the half-life of elinogrel (range of mean values: 9 to 16 hours) and the known pharmacokinetic inter- and intra-subject variability associated with elinogrel.

All subjects were planned to receive the following five treatments in a randomized order:

Treatment T1 (Variant 001): IR (Immediate release) tablet containing pH-modifying alkalizing agent, 150 mg.

Treatment T2 (Variant 002): Enteric-coated tablet, 150 mg.

Treatment T3 (Variant 003): Standard IR tablet, 150 mg.

Treatment T4 (Variant 004): IR capsule, closely matching Portola MF capsule formulation, 2×75 mg.

Treatment R (Reference): Portola MF capsule formulation, 2×75 mg.

A five treatment Russell "nearly" balanced Latin Square design was used to achieve better robustness to compensate for subject drop out. Subjects were randomized to one of the five Russell "nearly" balanced Latin Square sequences in equal numbers. Eligible subjects were randomized into one of the following treatment sequences given below in Table 30.

TABLE 30

Treatment sequences

| | Period 1 | Period 2 | Period 3 | Period 4 | Period 5 |
|---|---|---|---|---|---|
| Sequence I | T1 | T2 | T3 | T4 | R |
| Sequence II | T2 | T4 | R | T3 | T1 |
| Sequence III | T3 | R | T2 | T1 | T4 |
| Sequence IV | T4 | T3 | T1 | R | T2 |
| Sequence V | R | T1 | T4 | T2 | T3 |

At each baseline (Day −1), subjects were asked to fast overnight (for at least 10 hours prior to dosing) and continue to fast until 4 hours post-dose. Pharmacokinetic assessments were performed starting at pre-dose (0 h, Day 1) and continuing up until 72 hours post-dose. Subjects were domiciled at least 12 hours prior to dosing through to at least 24 hours post-dose for PK sample collection, at which time they were discharged from the study center. Safety assessments were performed up to 48 hours post-dose. Subjects were then asked to return to the study center on the next 2 mornings to complete the remaining PK sample collection period (i.e., 48 and 72 hours post-dose samples).

Study completion evaluations were performed following the 72-hour pharmacokinetic blood draw in the last treatment period, or in case of early termination.

Treatment with an immediate release tablet of Example 12 described in U.S. Patent Application No. 61/294,385 (see also WO/2011/088152) containing pH-modifying alkalizing agent, 150 mg in fasted state.

Treatment with an immediate release tablet of Example 13 described in U.S. Patent Application No. 61/294,385 (see also WO/2011/088152) not containing pH-modifying alkalizing agent, 150 mg in fasted state Treatment with 2×IR capsule of Example 2 described in U.S. Patent Application No. 61/294,385 (see also WO/2011/088152) 2×75 mg (150 mg) in fasted state.

Treatment with 2×IR capsule of Example 6 (Reference): 2×75 mg (150 mg) in fasted state.

TABLE 31

Plasma PK parameters of elinogrel following oral administration of a single 150 mg dose of elinogrel IR tablet with pH-modifier, enteric-coated tablet, standard IR tablet, IR capsule matching Portola MF capsule and Portola MF capsule formulation

| Treatment Group | Tmax (hr) | Cmax (ng/mL) | AUClast (hr*ng/mL) | AUCinf (hr*ng/mL) | CL/F (L/hr) | Vz/F (L) | T½ (hr) |
|---|---|---|---|---|---|---|---|
| T1 | 5.00 | 2304 | 16730 | 17220 | 11.2 | 107 | 7.33 |
| (N = 37-38) | (3.0; 10) | (767) | (7842) | (7861) | (6.44) | (46.4) | (2.25) |
| T2 | 6.00 | 1160 | 9547 | 9847 | 24.2 | 222 | 7.46 |
| (N = 36-37) | (3.0; 12.0) | (588) | (6521) | (6433) | (21.0) | (128) | (2.65) |
| T3 | 5.00 | 2195 | 17000 | 17430 | 14.6 | 118 | 7.03 |
| (n = 39-40) | (3.0; 10.0) | (1448) | (10792) | (10980) | (17.2) | (74.8) | (2.43) |
| T4 | 5.00 | 2303 | 16590 | 16900 | 16.6 | 137 | 7.18 |
| (N=40) | (2.0; 8.0) | (1135) | (10173) | (10198) | (26.1) | (124) | (2.17) |
| R | 5.00 | 4201 | 27590 | 27950 | 8.30 | 83.5 | 8.02 |
| (n=39) | (2.0; 8.0) | (2323) | (15399) | (15402) | (7.08) | (58.1) | (2.88) |

Mean and SD are presented for all parameters except for Tmax in which median values are shown
T1 = IR tablet with pH-modifier (150 mg), T2 = Enteric coated tablet (150 mg), T3 = IR tablet (150 mg), T4 = Novartis IR capsule (2 × 75 mg), R = Portola MF capsule (2 × 75 mg)
The Reference (R) capsule formulation gave the highest exposure after administration of a single oral dose.

For the statistical analysis of the PK parameters point estimates and the associated 90% confidence intervals for the test/reference ratios were calculated. The statistical comparisons are shown in Table 2 below.

Statistical Comparison of PK Parameters

Statistical comparisons of PK parameters of elinogrel following oral administration of a single 150 mg dose of elinogrel IR tablet with pH-modifier, immediate release (IR) tablet, enteric coated tablet, IR tablet, Novartis IR capsule and Portola MF capsule formulation

| PK parameter | Treatment | Adjusted Geometric Mean | Geometric Mean ratio | 90% CI | P-value |
|---|---|---|---|---|---|
| AUClast (hr * ng/mL) | R | 22590 | | | |
| | T1 | 15004 | 0.66 | (0.55, 0.80) | <.001 |
| | T2 | 7259 | 0.32 | (0.27, 0.39) | <.001 |
| | T3 | 13662 | 0.60 | (0.50, 0.73) | <.001 |
| | T4 | 12988 | 0.57 | (0.48, 0.69) | <.001 |
| AUCinf | R | 22969 | | | |

-continued

| PK parameter | Treatment | Adjusted Geometric Mean | Geometric Mean ratio | 90% CI | P-value |
|---|---|---|---|---|---|
| (hr * ng/mL) | T1 | 14992 | 0.65 | (0.55, 0.78) | <.001 |
| | T2 | 7475 | 0.33 | (0.27, 0.39) | <.001 |
| | T3 | 14207 | 0.62 | (0.52, 0.74) | <.001 |
| | T4 | 13340 | 0.58 | (0.49, 0.69) | <.001 |
| Cmax (ng/mL) | R | 3545 | | | |
| | T1 | 2186 | 0.62 | (0.52, 0.73) | <.001 |
| | T2 | 1005 | 0.28 | (0.24, 0.33) | <.001 |
| | T3 | 1864 | 0.53 | (0.45, 0.62) | <.001 |
| | T4 | 1944 | 0.55 | (0.47, 0.64) | <.001 |

T1 = IR tablet with pH-modifier (150 mg),
T2 = Enteric coated tablet (150 mg),
T3 = IR tablet (150 mg),
T4 = Novartis IR capsule (2 × 75 mg),
R = Portola MF capsule (2 × 75 mg)

Based on geometric mean ratios, relative bioavailability of elinogrel from the IR tablet with pH modifier was closest to the Portola MF capsule formulation after administration of a single oral dose

TABLE 32

PK results of the human pharmacokinetic study

| Formulation | Example no. | N | Tmax* h | Cmax ng/ml | CV % | AUClast ng*h/ml | CV % |
|---|---|---|---|---|---|---|---|
| HPMC Capsules (polymorph B) without MgO 2*75 mg | 6 | 36-37 | 5 | 4'201 | 55 | 27'590 | 55 |
| Film-coated tablet (polymorph A) with MgO 150 mg | 12 (U.S. application Ser. No. 61/294,385) | 39-40 | 5 | 2'304 | 33 | 16'730 | 46 |
| Film-coated tablet (polymorph A) without MgO 150 mg | 13 (U.S. application Ser. No. 61/294,385) | 39 | 5 | 2'195 | 66 | 17'000 | 63 |
| HPMC Capsule (polymorph A) without MgO 2*75 mg | 2 (U.S. application Ser. No. 61/294,385) | 37-38 | 5 | 2'303 | 49 | 16'590 | 61 |

Comparison of pharmacokinetic effects in human studies for polymorphic form B, A and D of the potassium salt of elinogrel.

There is an about 2-fold range in the bioavailability (AUC) of the 150 mg dose observed between the different polymorphs of the potassium salt of elinogrel (AUC [ng*h/ml] polymorph A: 17'000, B: 27590 and D: 35227). Therefore the polymorphic form does have a strong impact on the bioavailability of the drug. It is not obvious that the thermodynamically most stable polymorph D has the highest solubility and also the highest bioavailability of the 3 polymorphs (MADHU PUDIPEDDI, ABU T. M. SERAJUDDIN, JOURNAL OF PHARMACEUTICAL SCIENCES, VOL. 94, NO. 5, MAY 2005 page 929).

Elinogrel potassium salt polymorph D according to the present invention being the thermodynamically most stable polymorph results in higher bioavailability compared to polymorph A and B of the elinogrel potassium salt. The bioavailability is measured in a human study according to FDA guidelines for conducting bioavailability studies. The area under the curve (AUC) of elinogrel potassium salt polymorph. D results in at least 5% higher AUC, or in at least 10% higher AUC and or in at least 15% higher AUC, compared to other polymorphs of the elinogrel potassium salt.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A compound, of formula (I):

(I)

in a crystalline anhydrous form, wherein said form has at least one of the following characteristics:
   (a) an X-ray powder diffraction pattern with peaks at 11.2, 15.8, and 26.4 degrees two theta (±0.2 degree) (CuK$_\alpha$ λ=1.54059 Å), or an X-ray powder diffraction pattern substantially in accordance with that shown in FIG. 1;
   (b) a differential scanning calorimetry (DSC) melting followed by decomposition with an onset temperature of about 324° C. or a differential scanning calorimetry thermogram (DSC) substantially in accordance with that shown in FIG. 2;
   (c) an FT-IR spectrum with the bands at 3427, 1716, 1637, 1514 and 1240 cm$^{-1}$, or an FT-IR spectrum substantially in accordance with that shown in FIG. 3;
   (d) an FT-Raman spectrum with the bands at 1216, 1176, 699, 343 and 133 cm$^{-1}$ or a FT-Raman spectrum substantially in accordance with that shown in FIG. 4; or
   (e) shifts at about 165.7, 152.3, 146.4, 141.2, 130.2, and 112.8 ppm (±0.2 ppm) when characterized by $^{13}$C solid state NMR.

2. The compound of claim 1, characterized by an X-ray powder diffraction pattern which
   (i) has peaks at 1.2, 15.8, and 26.4 degrees two theta (±0.2 degree) (CuK$_\alpha$ λ1=1.54059 Å) or
   (ii) has peaks at 11.2, 15.8, 17.2, 19.1, 24.8, 25.6, 26.4, 28.8, 29.4 and 32.0 degrees two theta (±0.2 degree) (CuK$_\alpha$ λ=1.54059 Å), or
   (iii) is as depicted in FIG. 1.

3. The compound of claim 1, characterized by an FT-Raman spectrum which
   (a) has bands at 3427, 1716, 1637, 1514 and 1240 cm$^{-1}$, or
   (b) has bands at 1715, 1632, 1421, 1313, 1216, 1176, 919, 699, 343 and 133 cm$^{-1}$; or
   (c) is substantially in accordance with that shown in FIG. 4.

4. The compound of claim 1, which shows shifts at
   (a) 165.7, 152.3, 146.4, 141.2, 130.2, and 112.8 ppm (±0.2 ppm) when characterized by $^{13}$C solid state NMR; or
   (b) about 165.7, 152.3, 146.4, 141.2, 130.2, 112.8, 101.0, 97.0, and 31.4 ppm (±0.2 ppm) when characterized by $^{13}$C solid state NMR.

5. The compound of claim 1 in 99, 95, 90, 85, 80, 75, 70, or 65% purity.

6. A pharmaceutical composition comprising the compound according to claim 1 and one or more pharmaceutically acceptable carrier or excipient.

7. The pharmaceutical composition according to claim 6, comprising an additional therapeutic agent.

8. A solid pharmaceutical composition comprising the compound of claim 1 and at least one pharmaceutically acceptable carrier.

9. The solid pharmaceutical composition according to claim 8 which is in the form of a tablet or a capsule.

10. A compressed solid oral dosage form comprising: a) solid pharmaceutical composition comprising: a) at least about 15% the compound of claim 1, thereof by weight relative to the total weight of the overall pharmaceutical composition, and b) at least one pharmaceutically acceptable carrier.

11. The compressed solid dosage form according to claim 10 comprising the compound of claim 2 in a unit dosage of from between about 50 and 300 mg.

12. The compressed solid dosage form according to claim 11 comprising the compound of claim 2 in a unit dosage of from between about 75 and 100 mg.

13. The compressed solid dosage form according to claim 11 comprising the compound of claim 2 in a unit dosage of about 150 mg.

14. A process for preparing the compound according to claim 1 comprising the steps of:
   (a) adding, at a temperature between 20-30° C., an aqueous solution of a base, containing between 2.1 and 2.5 molar equivalents of a base, to a suspension of the acid of formula (II)

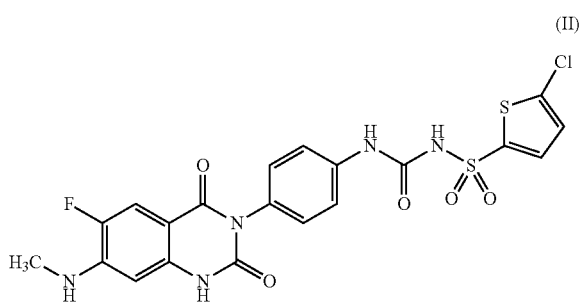 [SMILES: CNc1cc2[nH]c(=O)n(-c3ccc(NC(=O)NS(=O)(=O)c4ccc(Cl)s4)cc3)c(=O)c2cc1F]

(II)

in water, wherein the suspension is initially at a temperature between 20-30° C.;

(b) heating the resulting solution to a temperature between 40-50° C.;

(c) filtering the resulting solution at a temperature between 40-50° C.;

(d) adding, at a temperature between 40-50° C., methanol or a 50-90% w/w methanol/water mixture, to form a supersaturated solution;

(e) adding, over a period of at least two hours, an aqueous acidic solution, containing 1 molar equivalent less than the amount of base used in step (a), to the supersaturated solution, wherein the acid has a pKa in the range of 3-6; wherein the temperature is kept at a temperature between 40-50° C.;

(f) cooling the resulting suspension from a temperature in the range of 40-50° C. to a temperature in the range of 20-30° C. over a period of at least 1.5 hours;

(g) separating and washing the crystals obtained at the end of step (f); and (h) optionally drying the crystals.

\* \* \* \* \*